United States Patent
Shiraishi et al.

[11] Patent Number: 6,096,780
[45] Date of Patent: Aug. 1, 2000

[54] QUATERNARY AMMONIUM SALTS AND THEIR USE

[75] Inventors: Mitsuru Shiraishi, Hyogo; Masanori Baba, Kagoshima; Yoshio Aramaki, Hyogo; Osamu Nishimura, Ibaraki; Naoyuki Kanzaki, Osaka, all of Japan

[73] Assignee: Takeda Chemical Industries, Ltd., Osaka, Japan

[21] Appl. No.: 09/377,040

[22] Filed: Aug. 19, 1999

Related U.S. Application Data

[60] Provisional application No. 60/104,845, Oct. 16, 1998.

[30] Foreign Application Priority Data

Aug. 20, 1998 [JP] Japan ................. 10-234388

[51] Int. Cl.$^7$ .............. A61K 31/38; A61K 31/335; A61K 31/165; C07D 337/12; C07D 313/00
[52] U.S. Cl. .............. 514/431; 514/450; 514/617; 549/12; 549/355; 564/180
[58] Field of Search .............. 564/180; 549/355, 549/12; 514/617, 450, 431

[56] References Cited

U.S. PATENT DOCUMENTS 5,922,771  7/1999  Ohkawa et al. .............. 514/630
6,013,809  1/2000  Zimmer et al. .............. 549/9

FOREIGN PATENT DOCUMENTS

96/01267  1/1996  WIPO .

OTHER PUBLICATIONS

English Abstract of JP–A–25756/1995.
English Abstract of JP–A–25757/1995.
M. Baba et al. "A small–molecule, nonpeptide, CCR5 antagonist with highly potent and selective anti–HIV–1 activity", Proc. Natl. Acad. Sci., vol. 96, pp. 5698–5703, May 1999.

*Primary Examiner*—Deborah C. Lambkin
*Attorney, Agent, or Firm*—Wenderoth, Lind & Ponack, LLP.

[57] ABSTRACT

This invention is to provide a compound for antagonizing CCR5, said compound being represented by the formula:

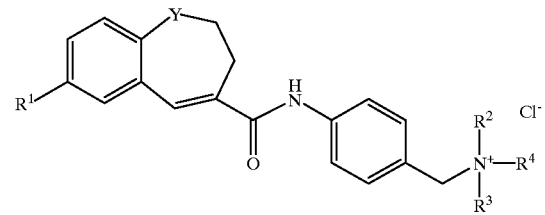

wherein $R^1$ is an optionally substituted phenyl or an optionally substituted thienyl; Y is —$CH_2$—, —S— or —O—; and $R^2$, $R^3$ and $R^4$ are independently an optionally substituted aliphatic hydrocarbon group or an optionally substituted alicyclic heterocyclic ring group, and being effective for the prevention and treatment of infectious disease of HIV.

22 Claims, No Drawings

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 1
caggatccga tggattatca agtgtcaagt ccaa                               34

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
tctagatcac aagcccacag atatttcctg ctcc                               34
```

QUATERNARY AMMONIUM SALTS AND THEIR USE

This application claims the benefit of U.S. provisional application No. 60/104,845, filed on Oct. 16, 1998.

TECHNICAL FIELD

The present invention relates to a quaternary ammonium salt which has CCR5 antagonistic activity and which is used for the treatment or prevention of infectious disease of HIV, etc.

BACKGROUND ART

Recently, HIV (human immunodeficiency virus) protease inhibitors are developed for method of the treatment of AIDS (acquired immunological deficient syndrome) and use of the protease inhibitors in combination with conventional two HIV reverse transcriptase inhibitors provides with a further progress of the treatment of AIDS. However, these drugs and their combination use are not sufficient for the eradication of AIDS, and development of new anti-AIDS drugs having different activity and mechanism are sought for.

As a receptor from which HIV invades to a target cell, CD4 is so far known, and recently CCR5 as a second receptor of macrophage-tropic HIV and CXCR4 as a second receptor of T cell-tropic HIV, each of which is G protein-coupled chemokine receptor having seven transmembrane domains, are respectively found out. These chemokine receptors are thought to play an essential role in establishment and spread of HIV infection. In fact, it is reported that a person who is resistant to HIV infection in spite of several exposures retains mutation of homo deletion of CCR5 gene. Therefore, a CCR5 antagonist is expected to be a new anti-HIV drug. However, so far, there has been no report that a CCR5 antagonist is developed as a therapeutic agent of AIDS.

DISCLOSURE OF INVENTION

The present invention is to provide a quaternary ammonium salt having CCR5 antagonistic activity and less toxicity; and a composition for antagonizing CCR5 (a drug for the treatment or prevention of infectious disease of HIV (in particular, AIDS), etc.) comprising said quaternary ammonium salt.

The present inventors diligently made extensive studies on compounds having CCR5 antagonistic activity and less toxicity, as a result, they found that a quaternary ammonium salt of the following formula (I) [hereinafter, referred to as Compound (I)] unexpectedly possesses potent CCR5 antagonistic activity and clinically desirable pharmaceutical effect (e.g. remarkable inhibition of HIV infection to human peripheral mononuclear cells, etc.) and also that Compound (I) has superior solubility, physicochemical properties (stability, anti-coloring effect, etc.), etc. and is useful for applying as an injection. Based on the finding, the present invention was accomplished.

More specifically, the present invention relates to (1) a compound of the formula:

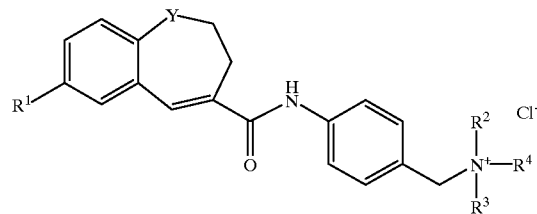

wherein $R^1$ is an optionally substituted phenyl or an optionally substituted thienyl; Y is —$CH_2$—, —S— or —O—; and $R^2$, $R^3$ and $R^4$ are independently an optionally substituted aliphatic hydrocarbon group or an optionally substituted alicyclic heterocyclic ring group; or a pro-drug thereof;

(2) a compound of the above (1), wherein $R^2$ and $R^3$ are independently an optionally substituted acyclic hydrocarbon group;

(3) a compound of the above (1), wherein $R^2$ and $R^3$ are independently an optionally substituted alkyl group;

(4) a compound of the above (1), wherein $R^4$ is an optionally substituted alicyclic hydrocarbon group or an optionally substituted alicyclic heterocyclic ring group;

(5) a compound of the above (4), wherein the alicyclic hydrocarbon group is cycloalkyl;

(6) a compound of the above (4), wherein the alicyclic hydrocarbon group is cyclohexyl;

(7) a compound of the above (4), wherein the alicyclic heterocyclic ring group is a saturated alicyclic heterocyclic ring group;

(8) a compound of the above (4), wherein the alicyclic heterocyclic ring group is tetrahydropyranyl, tetrahydrothiopyranyl or piperidyl;

(9) N,N-Dimethyl-N-(4-(((2-(4-methylphenyl)-6,7-dihydro-5H-benzocyclohepten-8-yl)carbonyl)amino)benzyl)-N-(4-tetrahydropyranyl)ammonium chloride;

(10) N,N-Dimethyl-N-(((7-(4-methylphenyl)-2,3-dihydro-1-benzoxepin-4-yl)carbonyl)amino)benzyl)-N-(4-oxocyclohexyl)ammonium chloride;

(11) N-(4-(((7-(4-Ethoxyphenyl)-2,3-dihydro-1-benzoxepin-4-yl)carbonyl)amino)benzyl)-N,N-dimethyl-N-(4-tetrahydropyranyl)ammonium chloride;

(12) a pharmaceutical composition which comprises a compound of the above (1);

(13) a pharmaceutical composition for antagonizing CCR5 which comprises a compound of the above (9);

(14) a composition of the above (13), which is for the treatment or prevention of infectious disease of HIV;

(15) a composition of the above (13), which is for the treatment or prevention of AIDS;

(16) a composition of the above (13), which is for the prevention of the progression of AIDS;

(17) a composition of the above (13), which is used in combination with a protease inhibitor and/or a reverse transcriptase inhibitor;

(18) a composition of the above (17), wherein the reverse transcriptase inhibitor is zidovudine, didanosine, zalcitabine, lamivudine, stavudine, nevirapine, delavirdine, efavirenz or abacavir;

(19) a composition of the above (17), wherein the protease inhibitor is saquinavir, ritonavir, indinavir or nelfinavir;

(20) use of the compound of the above (9) in combination with a protease inhibitor and/or a reverse transcriptase inhibitor for the treatment or prevention of infectious disease of HIV; etc.

In the above formula (I), example of the "substituents" which the "phenyl group" and the "thienyl group" of the "optionally substituted phenyl group" and "optionally substituted thienyl group" represented by $R^1$ may have include halogen atom, nitro, cyano, an optionally substituted alkyl, an optionally substituted cycloalkyl, an optionally substituted hydroxy group, an optionally substituted thiol group, an optionally substituted amino group, an optionally substituted acyl, an optionally esterified carboxyl group, an optionally substituted aromatic group, etc.

Examples of the halogen as the substituents for $R^1$ include fluorine, chlorine, bromine, iodine, etc. Among others, fluorine and chlorine are preferable.

Examples of the alkyl in the optionally substituted alkyl as the substituents for $R^1$ include a straight or branched $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$) alkyl.

Examples of the substituents in the optionally substituted alkyl include halogen (e.g. fluorine, chlorine, bromine, iodine, etc.), nitro, cyano, hydroxy group, thiol group, amino group, carboxyl group, an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the cycloalkyl in the optionally substituted cycloalkyl as the substituents for $R^1$ include $C_{3-7}$ cycloalkyl, etc. such as cyclopropyl, cyclobutyl, cyclopentyl, cyclohexyl, cycloheptyl, etc.

Examples of the substituents in the optionally substituted cycloalkyl include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted hydroxy group as the substituents for $R^1$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted aralkyl (e.g. phenyl-$C_{1-4}$ alkyl (e.g. benzyl, phenethyl, etc.), etc.);

(6) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.); etc.

Examples of the substituents which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl and (7) optionally substituted aryl may have include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted thiol group as the substituents for $R^1$ are the same as the above-described substituents in the optionally substituted hydroxy group as the substituents for $R^1$, and among others, (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted aralkyl (e.g. phenyl-$C_{1-4}$ alkyl (e.g. benzyl, phenethyl, etc.), etc.);

(4) an optionally substituted aryl (e.g. phenyl, naphthyl, etc.); etc. are preferable.

Examples of the substituents which the above-mentioned (1) optionally substituted alkyl, (2) optionally substituted cycloalkyl, (3) optionally substituted aralkyl and (4) optionally substituted aryl may have include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted amino group as the substituents for $R^1$ are the same as the above-described substituents in the optionally substituted hydroxy group as the substituents for $R^1$, and examples of the optionally substituted amino group as the substituents for $R^1$ include an amino group which may have one to two substituents selected from the above-described substituents in the optionally substituted hydroxy group as the substituents for $R^1$, etc. Among others, as the substituents in the optionally substituted amino group as the substituents for $R^1$, (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(6) an optionally substituted aryl (e.g. phenyl, naphthyl, etc.); etc. are preferable.

Examples of the substituents, which each of the above-described (1) optionally substituted alkyl, (2) optionally substituted cycloalkyl, (3) optionally substituted alkenyl, (4) optionally substituted cycloalkenyl, (5) optionally substituted acyl and (6) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

The substituents in the optionally substituted amino group as the substituents for $R^1$ may bind to each other to form a cyclic amino group (e.g. 5- to 6-membered cyclic amino, etc. such as pyrrolidine, pyrroline, piperazine, piperidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally substituted acyl as the substituents for $R^1$ include a carbonyl group or a sulfonyl group binding to (1) hydrogen;

(2) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(3) an optionally substituted cycloalkyl (e.g. $C_{3-7}$ cycloalkyl, etc. such as cyclopropyl, cyclobutyl, cyclopentyl, cyclohexyl, cycloheptyl, etc.);

(4) an optionally substituted alkenyl (e.g. $C_{2-10}$ alkenyl such as allyl, crotyl, 2-pentenyl,3-hexenyl, etc., preferably lower ($C_{2-6}$) alkenyl, etc.);

(5) an optionally substituted cycloalkenyl (e.g. $C_{3-7}$ cycloalkenyl, etc. such as 2- cyclopentenyl, 2-cyclohexenyl, 2-cyclopentenylmethyl, 2-cyclohexenylmethyl, etc.);

(6) an optionally substituted 5- to 6-membered monocyclic aromatic group (e.g. phenyl, pyridyl, etc.); etc.

Examples of the acyl include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl, etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted 5- to 6-membered monocyclic aromatic group may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally esterified carboxyl group as the substituents for $R^1$ include a carbonyloxy group binding to (1) hydrogen;

(2) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(3) an optionally substituted cycloalkyl (e.g. $C_{3-7}$ cycloalkyl, etc. such as cyclopropyl, cyclobutyl, cyclopentyl, cyclohexyl, cycloheptyl, etc.);

(4) an optionally substituted alkenyl (e.g. $C_{2-10}$ alkenyl such as allyl, crotyl, 2-pentenyl,3-hexenyl, etc., preferably lower ($C_{2-6}$) alkenyl, etc.);

(5) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(6) an optionally substituted aryl (e.g. phenyl, naphthyl, etc.); etc., and preferably carboxyl, lower ($C_{1-6}$) alkoxy-carbonyl, aryloxycarbonyl (e.g. methoxycarbonyl, ethoxycarbonyl, propoxycarbonyl, phenoxycarbonyl, naphthoxycarbonyl, etc.), etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the aromatic group in the optionally substituted aromatic group as the substituents for $R^1$ include 5- to 6-membered homocyclic or heterocyclic ring aromatic ring, etc. such as phenyl, pyridyl, furyl, thienyl, pyrrolyl, imidazolyl, pyrazolyl, thiazolyl, oxazolyl, isothiazolyl, isoxazolyl, tetrazolyl, pyrazinyl, pyrimidinyl, pyridazinyl, triazolyl, etc.

Examples of the substituents for these aromatic group include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

The number of the above-mentioned substituents for $R^1$ is 1–4 (preferably 1–2) and they may be same or different and present at any possible position on the ring represented by $R^1$. When two or more substituents are present on the "phenyl group" and the "thienyl group" of the "optionally substituted phenyl group" and "optionally substituted thienyl group" represented by $R^1$, two substituents among them may bind to each other to form a lower ($C_{1-6}$) alkylene (e.g. trimethylene, tetramethylene, etc.), a lower ($C_{1-6}$) alkyleneoxy (e.g. —CH$_2$O—CH$_2$—, —O—CH$_2$—CH$_2$—, etc.), a lower ($C_{1-6}$) alkylenedioxy (e.g. —O—CH$_2$—O—, —O—CH$_2$—CH$_2$—O—, etc.), a lower ($C_{2-6}$) alkenylene (e.g. —CH$_2$—CH=CH—, —CH$_2$—CH$_2$—CH=CH—, —CH$_2$—CH=CH—CH$_2$—, etc.), a lower ($C_{4-6}$) alkadienylene (e.g. —CH=CH—CH=CH—, etc.), etc.

Preferred examples of the "substituents", which the "phenyl group" and the "thienyl group" of the "optionally substituted phenyl group" and "optionally substituted thienyl group" represented by $R^1$ may have, include an optionally halogenated lower ($C_{1-4}$) alkyl (e.g. methyl, ethyl, t-butyl, trifluoromethyl, etc.), an optionally halogenated lower ($C_{1-4}$) alkoxy (e.g. methoxy, ethoxy, t-butoxy, trifluoromethoxy, etc.), halogen (e.g. fluorine, chlorine, etc.), nitro, cyano, an amino group optionally substituted with 1–2 lower ($C_{1-4}$) alkyl groups (e.g. amino, methylamino, dimethylamino, etc.), 5- to 6-membered cyclic amino (e.g. 1-pyrrolidinyl, 1-piperazinyl, 1-piperidinyl, 4-morpholino, 4-thiomorpholino, 1-imidazolyl, 4-tetrahydropyranyl, etc.), etc., and when R is a phenyl group, the "substituent" is preferably present at para position.

In the above formula (I), Y is —CH$_2$—, —S— or —O—; and preferably —CH$_2$— or —O—.

In the above formula (I), $R^2$, $R^3$ and $R^4$ are independently an optionally substituted aliphatic hydrocarbon group or an optionally substituted alicyclic heterocyclic ring group.

Examples of the "aliphatic hydrocarbon group" in the "optionally substituted aliphatic hydrocarbon group" represented by $R^2$, $R^3$ and $R^4$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-8}$ cycloalkyl, etc. such as cyclopropyl, cyclobutyl, cyclopentyl, cyclohexyl, cycloheptyl, cyclooctyl, etc.); provided that (3) an optionally substituted alkenyl (e.g. $C_{2-10}$ alkenyl such as allyl, crotyl, 2-pentenyl, 3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.); etc.

Examples of the "alicyclic heterocyclic ring group" in the "optionally substituted alicyclic heterocyclic ring group" represented by $R^2$, $R^3$ and $R^4$ include a 5- to 6-membered non-aromatic heterocyclic ring containing 1 to 4 hetero-atoms consisting of 1 to 2 kinds of hetero-atoms selected from oxygen atom, sulfur atom and nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; preferably a saturated 5- to 6-membered heterocyclic ring, etc., such as tetrahydrofuran, piperidine, tetrahydropyran, tetrahydrothiopyran, etc.); etc.

Examples of the substituents, which the "aliphatic hydrocarbon group" and the "alicyclic heterocyclic ring group" in the "optionally substituted aliphatic hydrocarbon group" and the "optionally substituted alicyclic heterocyclic ring group" represented by $R^2$, $R^3$ and $R^4$ may have, include halogen (e.g. fluorine, chlorine, bromine, iodine, etc.), an optionally halogenated lower ($C_{1-4}$) alkyl, an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), phenyl, phenyl-lower ($C_{1-4}$) alkyl, $C_{3-7}$ cycloalkyl, cyano, nitro, oxo, hydroxy group, thiol group, amino group, carboxyl group, lower ($C_{1-4}$) alkoxy-carbonyl (preferably, halogen, an optionally halogenated lower ($C_{1-4}$) alkyl, an optionally halogenated lower ($C_{1-4}$) alkoxy, phenyl-lower ($C_{1-4}$) alkyl, $C_{3-7}$ cycloalkyl, cyano, oxo, hydroxy group, etc.), etc., and the number of the substituents are preferably 1 to 3.

In the above formula (I), as the group $R^2$ or $R^3$, an optionally substituted acyclic hydrocarbon group is preferable, an optionally substituted alkyl group is more preferable. In particular, the groups $R^2$ and $R^3$ are preferably the same and more preferably both of the groups $R^2$ and $R^3$ are methyl.

In the above formula (I), as the group $R^4$, an optionally substituted alicyclic hydrocarbon group or an optionally substituted alicyclic heterocyclic ring group and more preferably an optionally substituted cycloalkyl group or an optionally substituted saturated alicyclic heterocyclic ring group. In particular, $R^4$ is preferably an optionally substituted cyclohexyl or an optionally substituted 6-membered saturated alicyclic heterocyclic ring group and more preferably an optionally substituted cycloalkyl, an optionally substituted tetrahydropyranyl, an optionally substituted tetrahydrothiopyranyl or an optionally substituted piperidyl.

The compound of the formula (I) of the present invention may be hydrated or solvated. When the compound of the formula (I) of the present invention exists as configuration isomer, diastereomer, conformer, etc., it is possible to isolate individual isomers with per se known separation and purification method, if desired. When the compound of the formula (I) of the present invention is racemate, it can be separated into (S)-compound and (R)-compound with usual optical resolution and individual optical isomers and a mixture thereof are included in the scope of the present invention.

The pro-drug of Compound (I) means a compound which is converted to Compound (I) under the physiological condition or with a reaction due to an enzyme, an gastric acid, etc. in the living body, that is, a compound which is converted to Compound (I) with oxidation, reduction, hydrolysis, etc. according to an enzyme; a compound which is converted to Compound (I) with gastric acid, etc.; etc.

Examples of the pro-drug of Compound (I) include a compound wherein an amino group of Compound (I) is substituted with acyl, alkyl, phosphoric acid, etc. (e.g. a compound wherein an amino group of Compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of Compound (I) is substituted with acyl, alkyl, phosphoric acid, boric acid, etc. (e.g. a compound wherein an hydroxy group of Compound (I) is substituted with acetyl, palmitoyl, propanoyl, pivaloyl, succinyl, fumaryl, alanyl, dimethylaminomethylcarbonyl, etc.); a compound wherein a carboxyl group of Compound (I) is modified with ester, amide, etc. (e.g. a compound wherein a carboxyl group of Compound (I) is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drug can be produced by per se known method from Compound (I).

The pro-drug of Compound (I) may be a compound which is converted into Compound (I) under the physiological conditions as described in "Pharmaceutical Research and Development", Vol. 7 (Drug Design), pages 163–198 published in 1990 by Hirokawa Publishing Co. (Tokyo, Japan).

Compound (I) may be labeled with isotope (e.g. $^3$H, $^{14}$C, $^{35}$S, $^{125}$I, etc.), etc.

The present compound of the formula (I) alone or as an admixture with a pharmaceutically acceptable carrier may be non-orally administered as a liquid preparation such as an injection.

Examples of the carriers include various organic or inorganic carriers which are generally used in this field. For example, a solvent, a solubilizer, a suspending agent, a isotonizing agent, a buffer, a soothing agent, etc. are used in the liquid formulations. In addition, if desired, an appropriate additive such as a preservative, an antioxidant, a colorant, a sweetener, etc. may be used in the above formulations.

Examples of the solvent include water for injection, alcohol, propyleneglycol, macrogol, sesame oil, corn oil, etc. Examples of the solubilizer include polyethyleneglycol, propyleneglycol, polyoxyethylene (20) sorbitan monooleate (polysorbate 80), D-mannitol, benzyl benzoate, ethanol, trisaminomethane, cholesterol, triethanolamine, sodium carbonate, sodium citrate, etc. Examples of the suspending agent include surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc.; etc. Examples of the isotonizing agent include sodium chloride, glycerin, D-mannitol, etc. Examples of the buffer include a buffer solution of phosphate, acetate, carbonate, citrate, etc. Examples of the soothing agent include benzylalcohol, etc. Examples of the preservative include paraoxybenzoic acid esters, chlorobutanol, benzylalcohol, phenethylalcohol, dehydroacetic acid, sorbic acid, etc. Examples of the antioxidant include sulfites, ascorbic acid, etc.

The compound of the formula (I) of the present invention may be used in combination with other drug for the treatment or prevention of infectious disease of HIV (in particular, a pharmaceutical composition for the treatment or prevention of AIDS). In this case, these drugs can be formulated by mixing individually or simultaneously with pharmaceutically acceptable carriers, excipients, binders, diluents or the like, which can be administered non-orally as a pharmaceutical composition for the treatment or prevention of infectious disease of HIV. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g. a diluent when administered (e.g. a kit for injection which comprises two or more ampoules each comprising a powdery component and a diluent for mixing and dissolving two or more components when administered, etc.), etc. are also included by the pharmaceutical composition of the present invention.

Example of the other pharmaceutical agent for the treatment or prevention of infectious disease of HIV to be used in combination with the compound of the formula (I) of the present invention include nucleoside reverse transcriptases inhibitor such as zidovudine, didanosine, zalcitabine, lamivudine, stavudine, abacavir, adefovir, adefovir dipivoxil, fozivudine tidoxil, etc.; non-nucleoside reverse transcriptases inhibitor (including an agent having antioxidation activity such as immunocal, oltipraz, etc.) such as nevirapine, delavirdine, efavirenz, loviride, immunocal, oltipraz, etc.; protease inhibitors such as saquinavir, ritonavir, indinavir, nelfinavir, amprenavir, palinavir, lasinavir, etc.; etc.

As the nucleoside reverse transcriptase inhibitor, zidovudine, didanosine, zalcitabine, lamivudine, stavudine, etc. are preferable; as the non-nucleoside reverse transcriptase inhibitor, nevirapine, delavirdine, etc. are preferable; and as the protease inhibitor, saquinavir, ritonavir, indinavir, nelfinavir, etc. are preferable.

The compound of the formula (I) can be produced in accordance with per se known methods, for example, the methods described below, the methods described in JP-A-73476/1996, or analogous methods thereto.

A salt of the compound of the formulas (I), (II), (III), (IV), (V), (I-1), (I-2) and (I-3) may form a salt with inorganic base, organic base, inorganic acid, organic acid, basic or acidic amino acid, etc., as long as such a salt does not interfere the reaction. Examples of the salt with the inorganic base include a salt with alkali metal (e.g. sodium, potassium, etc.), alkaline earth metal (e.g. calcium, magnesium, etc.), aluminum, ammonium, etc. Examples of the salt with the organic base include a salt with trimethylamine, triethylamine, pyridine, picoline, ethanolamine, diethanolamine, triethanolamine, dicyclohexylamine, N,N'-dibenzylethylenediamine, etc. Examples of the salt with the inorganic acid include a salt with hydrochloric acid, hydrobromic acid, nitric acid, sulfuric acid, phosphoric acid, etc. Examples of the salt with the organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Examples of the salt with the basic amino acid include a salt with arginine, lysine, ornithine, etc. Examples of the salt with the acidic amino acid include a salt with aspartic acid, glutamic acid, etc.

In the following reaction steps, when the starting compounds have, as substituents, an amino group, a carboxyl group and/or hydroxy group, these groups may be protected by ordinary protective groups such as those generally employed in peptide chemistry, etc. After the reaction, if necessary, the protective groups may be removed to obtain the desired compound.

Examples of the amino-protective group include an optionally substituted formyl, an optionally substituted $C_{1-6}$ alkyl-carbonyl (e.g. methylcarbonyl, ethylcarbonyl, etc.), phenylcarbonyl, $C_{1-6}$ alkyloxy-carbonyl (e.g. methoxycarbonyl, ethoxycarbonyl, t-butoxycarbonyl, etc.), aryloxycarbonyl (e.g. phenoxycarbonyl, etc.), $C_{7-10}$ aralkyloxy-carbonyl (e.g. benzyloxycarbonyl, etc.), trityl, phthaloyl, etc. These protective groups may be substituted by 1 to 3 substituents such as halogen atom (e.g. fluorine, chlorine, bromine, iodine, etc.), $C_{1-6}$ alkyl-carbonyl (e.g. acetyl, propionyl, butyryl, etc.), nitro group, etc.

Examples of the carboxyl-protective group include an optionally substituted $C_{1-6}$ alkyl (e.g. methyl, ethyl, propyl, isopropyl, butyl, tert-butyl, etc.), phenyl, trityl, silyl, etc. These protective groups may be substituted by 1 to 3 substituents such as halogen atom (e.g. fluorine, chlorine, bromine, iodine, etc.), formyl, $C_{1-6}$ alkyl-carbonyl (e.g. acetyl, propionyl, butyryl, etc.), nitro group, etc.

Examples of the hydroxy-protective group include an optionally substituted $C_{1-6}$ alkyl (e.g. methyl, ethyl, propyl, isopropyl, butyl, tert-butyl, etc.), phenyl, $C_{7-10}$ aralkyl (e.g. benzyl, etc.), formyl, $C_{1-6}$ alkyl-carbonyl (e.g. acetyl, propionyl, etc.), phenyloxycarbonyl, $C_{7-10}$ aralkyloxy-carbonyl (e.g. benzyloxycarbonyl, etc.), pyranyl, furanyl, silyl, etc. These protective groups may be substituted by 1 to 4 substituents such as halogen atom (e.g. fluorine, chlorine, bromine, iodine, etc.), $C_{1-6}$ alkyl, phenyl, $C_{7-10}$ aralkyl, nitro group, etc.

These protective group may be introduced or removed by per se known methods (e.g. a method described in Protective Groups in Organic Chemistry (J. F. W. McOmie et al.; Plenum Press Inc.) or the methods analogous thereto. For example, employable method for removing the protective groups is a method using an acid, a base, reduction, ultraviolet ray, hydrazine, phenylhydrazine, sodium N-methyldithiocarbamate, tetrabutylammonium fluoride, palladium acetate, etc.

[Method A]

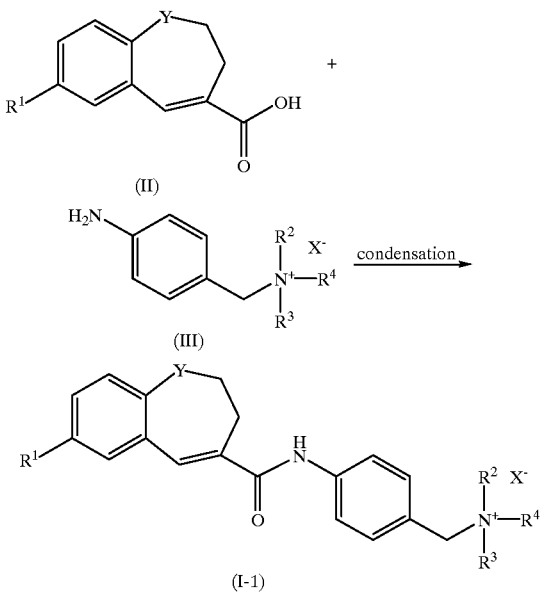

wherein X is an counter anion (e.g. an anion of a halogen atom (e.g. $Cl^-$, $Br^-$, $I^-$, etc.), etc.) and the other symbols are as defined above.

This production method is carried out by reacting the compound (II) with the aniline derivative (III) to obtain the anilide Compound (I-1).

The condensation reaction of the compounds (II) and (III) is carried out by usual methods for peptide synthesis. Said methods for peptide synthesis are employed according to optional known methods, for example, methods described in "Peptide Synthesis" written by M. Bodansky and M. A. Ondetti, Interscience, New York, 1966; "The Proteins", volume 2, written by F. M. Finn and K. Hofmann, H. Nenrath and R. L. Hill edition, Academic Press Inc., New York, 1976; "peputido-gosei no kiso to jikken (Basis and Experiment of Peptide Synthesis)" written by Nobuo Izumiya et al., Maruzen K. K. ,1985; etc., as well as azide method, chloride method, acid anhydride method, mixed acid anhydride method, DCC method, active ester method, method using Woodward reagent K, carbonyldiimidazole method, oxidation-reduction method, DCC/HONB method, etc. and in addition WSC method, method using diethyl cyanophosphate (DEPC), etc.

The condensation reaction can be carried out in a solvent. Examples of the solvents to be employed in the reaction include anhydrous or hydrous N,N-dimethylformamide (DMF), dimethylsulfoxide, pyridine, chloroform, dichloromethane, tetrahydrofuran, dioxane, acetonitrile, or a suitable mixture of these solvents. The reaction temperature is generally about $-20°$ C. to about 50° C., preferably about $-10°$ C. to about 30° C. and the reaction time is generally about 1 to about 100 hours, preferably about 2 to about 40 hours.

[Method B]

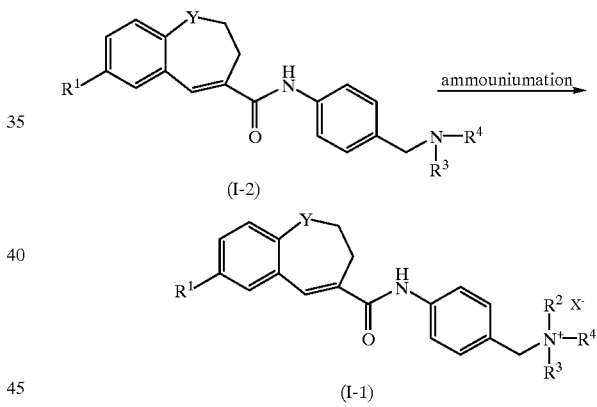

When Compound (I-2) has a tertiary amine residue, Compound (I-1) having an quaternary ammonium can be produced by reacting Compound (I-2) with halogenated alkyl. Examples of a halogen atom include chlorine, bromine, iodine, etc. and usually about 1 to 5 moles of the halogenated alkyl (e.g. halogenated lower ($C_{1-6}$) alkyl, etc.) is used per mole of Compound (I-2). The reaction is carried out in an inert solvent such as toluene, benzene, xylene, dichloromethane, chloroform, 1,2-dichloroethane, dimethylformamide, dimethylacetamide, etc., or a suitable mixture of these solvents. The reaction temperature is generally about 10° C. to about 160° C., preferably about 20 to about 120° C. and the reaction time is generally about 1 hour to about 100 hours, preferably about 2 hours to about 40 hours. This reaction is preferably carried out under inert gas (e.g. nitrogen, argon, etc.) atmosphere.

[Method C]

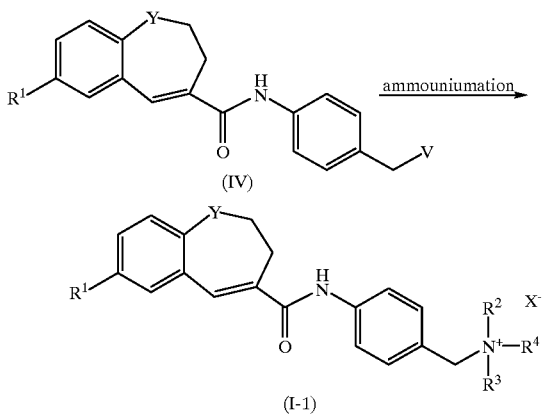

wherein V in the Compound (IV) is a halogen atom (chlorine, bromine, iodine, etc.), or a sulfonyloxy group (methane-sulfonyloxy group, trifluoromethanesulfonyloxy group, benzenesulfonyloxy group, toluenesulfonyloxy group, etc.), and the other symbols are as defined above.

Compound (I-1) having a quaternary ammonium can be produced by reacting Compound (IV) and a tertiary amine. The reaction is carried out in an inert solvent such as toluene, benzene, xylene, dichloromethane, chloroform, 1,2-dichloroethane, dimethylformamide (DMF), dimethylacetamide, etc., or a suitable mixture of these solvents. Usually, about 1–3 moles of the tertiary amine is used per mole of Compound (IV). The reaction temperature is generally about 10° C. to about 120° C., and the reaction time is generally about 1 hour to about 40 hours. This reaction is preferably carried out under inert gas (e.g. nitrogen, argon, etc.) atmosphere.

[Method D]

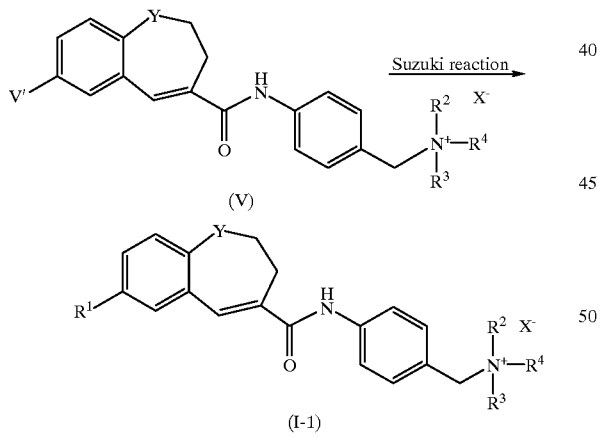

Compound (I-1) can be produced by subjecting Compound (V) wherein V' is a halogen atom (bromine, iodine, etc.) or a sulfonyloxy group (trifluoromethanesulfonyloxy group, etc.), and the other symbols are as defined above to, for example, Suzuki reaction [cross condensation reaction of aryl borate with e.g. aryl halide or aryloxytrifluoromethanesulfonate in the presence of palladium catalyst; A. Suzuki et al., Synth. Commun. 1981, 11, 513]. Usually, about 1–1.5 times moles of aryl borate is used per mole of Compound (V).

The thus obtained anilide derivative (I-1) can be isolated and purified by known separation and purification methods such as concentration, concentration under reduced pressure, extraction, crystallization, recrystallization, solvent convert, chromatography, etc.

If necessary, the thus obtained compound (I-1) can be converted into the desired compound (I) wherein X is chlorine by per se known method (e.g. a method using ion exchange resin, exchange reaction in a solvent containing an excess amount of sodium chloride, etc.).

Compound (II) used as a starting material can be produced by a known method (e.g. method described in JP-A-73476/1996, etc.) or the methods analogous thereto. For example, Compound (II) can be produced by a method described in the following Reaction Scheme I, a method described in the following Reference Examples or the methods analogous thereto.

Reaction Scheme I

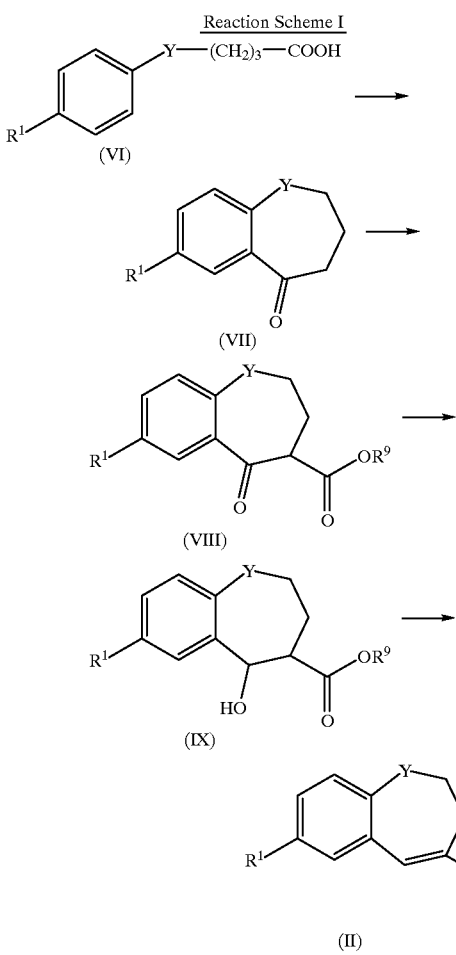

wherein $R^9$ is a $C_{1-4}$ alkyl group, and the other symbols are as defined above.

In this reaction, the compound of the formula (VI) is heated with a polyphosphoric acid, or Compound (VI) is converted to acid chloride with thionyl chloride, oxalyl chloride, phosphorous oxychloride, phosphorous pentachloride, etc., followed by subjecting the resulting acid chloride to usual Friedel-Crafts reaction and cyclizing the same to produce Compound (VII). Compound (VII) is reacted with carbonate ester in the presence of a base to produce ketoester (VIII). Compound (VIII) is subjected to reduction with catalytic hydrogenation or sodium boron hydride, etc. to produce Compound (IX). Compound (IX) is subjected to dehydration and ester hydrolysis by per se known methods to produce unsaturated carboxylic acid (II).

Compound (III) can be produced by a known method (e.g. method described in JP-A-73476/1996, etc.) or the methods analogous thereto. For example, Compound (III) can be produced by a method described in the following Reaction Scheme II, a method described in the following Reference Examples or the methods analogous thereto.

Reaction Scheme II

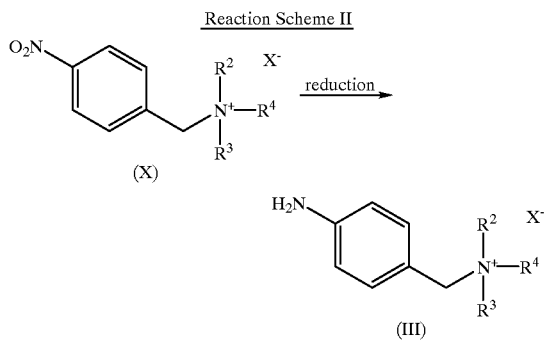

The reduction of Compound (X) can be carried out by per se known methods, for example, reduction with metal, reduction with metal hydride, reduction with metal hydride complex compound, reduction with diborane or substituted borane, catalytic hydrogenation, etc. That is, this reaction is carried out by treating Compound (X) with reduction agent. Examples of the reduction agent include metal such as reduced iron, zinc powder, etc.; alkali metal boron hydride (e.g. sodium boron hydride, lithium boron hydride, etc.); metal hydride complex compound such as aluminum lithium hydride, etc.; metal hydride such as sodium hydride etc.; organic tin compound (triphenyltin hydride, etc.), metal complex compound and metal salt such as nickel compound, zinc compound etc.; catalytic reduction agent using hydrogen and transit metal catalyst such as palladium, plutinum, rhodium, etc.; diborane; etc. Among others, as the reduction agent, catalytic reduction agent using hydrogen and transit metal catalyst such as palladium, plutinum, rhodium, etc.; reduced iron, etc. are preferable. The reaction is carried out in a solvent which does not inhibit the reaction. Examples of the solvent include benzene, toluene, xylene, chloroform, carbon tetrachloride, dichloromethane, 1,2-dichloroethane, 1,1,2,2-tetrachloroethane, diethylether, tetrahydrofuran, dioxane, methanol, ethanol, propanol, isopropanol, 2-methoxyethanol, N,N-dimethylformamide, acetic acid, or a suitable mixture of these solvents, etc. The solvent is appropriately selected depending on kind of the reduction agent. The reaction temperature is generally about −20° C. to about 150° C., preferably about 0° C. to about 100° C., and the reaction time is generally about 1 to about 24 hours.

The resulting Compound (III) can be separated and purified with know separation and purification methods such as concentration, concentration under reduced pressure, extraction, crystallization, was recrystallized with, solvent conversion, chromatography, etc.

The compound of the formula (I) of the present invention has potent CCR5 antagonistic activity and therefore can be used for the treatment or prevention of various infectious diseases of HIV, for example, AIDS in human. The compound of the formula (I) of the present invention is low toxic and safely used as CCR5 antagonist for the treatment or prevention of AIDS and also for the prevention of the progression of AIDS. The compound of the formula (I) of the present invention has superior solubility and absorbability, and therefore it can be advantageously used as injection.

The dose per day of the compound of the formula (I) varies depending on the condition and body weight of a patient, administration route, etc. Typical daily dose per adult patient (body weight: 50 Kg) for subcutaneous administration is about 1–200 mg, preferably about 1–100 mg, more preferably about 2–50 mg, and in particular about 5–30 mg, as active ingredient [the compound of the formula (I)] and the compound of the formula (I) is administered once or 2–3 times par day.

When the compound of the formula (I) is used in combination with a reverse transcriptase inhibitor and/or a protease inhibitor, the dose of the reverse transcriptase inhibitor or the protease inhibitor ranges, for example, from about 1/200–1/2 or more of usual dose to about 2–3 times or less of usual dose. In case that two or more drugs are used in combination, each dose of the drugs is appropriately adjusted if one drug affects metabolism of the other drug, while each dose of the drugs when they are used in combination is generally the same as the dose when they are used alone.

Typical daily dose of the reverse transcriptase inhibitor and the protease inhibitor is as follows:

| | |
|---|---|
| zidovudine | 100 mg |
| didanosine | 125–200 mg |
| zalcitabine | 0.75 mg |
| lamivudine | 150 mg |
| stavudine | 30–40 mg |
| saquinavir | 600 mg |
| ritonavi | 600 mg |
| indinavir | 800 mg |
| nelfinavir | 750 mg |

In case of combination use of the compound of the formula (I) with a reverse transcriptase inhibitor and/or a protease inhibitor preferred embodiments are shown below.

①  A drug containing about 1–200 mg of the compound of the formula (I) and a drug containing about 50–200 mg of zidovudine to one adult patient (body weight: 50 Kg) are administered. Each of the drugs may be administered to the one and the same subject simultaneously or with time intervals of 12 hours or less.

②  A drug containing about 1–200 mg of the compound of the formula (I) and a drug containing about 300–1200 mg of saquinavir to one adult patient (body weight: 50 Kg) are administered. Each of the drugs may be administered to the one and the same subject simultaneously or with time intervals of 12 hours or less.

BEST MODE FOR CARRYING OUT THE INVENTION

The present invention is hereinafter described in more detail by means of the following Test Example, Reference Example and Working Example, which are mere examples of the present invention and are not construed as limitative to the present invention.

The following gene manipulation is carried out in accordance with methods described in textbook (Maniatis et al., Molecular Cloning, Cold Spring Harbor Laboratory, 1989) or protocol attached to reagents.

Test Example
(1) Cloning of Human CCR5 Chemokine Receptor

Cloning of CCR5 gene was carried out by PCR (polymerase chain reaction) from human spleen cDNA. With using 0.5 ng of spleen cDNA (Toyobo, QUICK-Clone cDNA) as template, PCR was performed in DNA Thermal Cycler 480 (Perkin-Elmer) (reaction conditions: 30 cycles of 95° C. for 1 minute, 60° C. for 1 minute, and 75° C. for 5 minutes) by adding primer set, 5'-CAGGATCCGATGGATTATCAAGTGTCAAGTCCAA-3' (SEQ ID NO. 1) (25 pmol) and 5'-TCTAGATCACAAGCCCACAGATATTTCCTGCTCC-3' (SEQ ID NO. 2) (25 pmol), which were designed referring to nucleotide sequence of CCR5 gene reported by Samson et al. (Biochemistry, 35(11), 3362–3367 (1996)) and by using TaKaRa EX Taq (Takara Shuzo). The resultant PCR product was subjected to agarose gel electrophoresis to collect about 1.0 kb DNA fragment, which was subjected to Original TA Cloning Kit (Funakoshi) to carry out cloning of CCR5 gene.

(2) Preparation of Plasmid for Expression of Human CCR5

The plasmid obtained in the above (1) was digested with restriction enzymes XbaI (Takara Shuzo) and BamHI (Takara Shuzo) and subjected to agarose gel electrophoresis to collect about 1.0 kb DNA fragment. The DNA fragment was mixed with plasmid pcDNA3.1 (Funakoshi) for expression in animal cells, said plasmid being digested with XbaI and BamHI, and they were ligated with DNA Ligation Kit Ver.2 (Takara Shuzo). The resulting plasmid was subjected to transformation of competent cell of E. coli JM109 (Takara Shuzo) to obtain plasmid pCKR5.

(3) Introduction of Plasmid for Expression of Human CCR5 into CHO-K1 Cell and Expression of Plasmid for Expression of Human CCR5 in CHO-K1 Cell CHO-K1 cells were grown in 750 ml of tissue culture flask (Becton Dickinson) using Ham's F12 medium (Nihon Pharmaceutical) containing 10% fetal calf serum (Life Tech Oriental) and took off with 0.5 g/L trypsin-0.2 g/L EDTA (Life Tech Oriental). The cells were washed with PBS (Life Tech Oriental), centrifuged (1000 rpm, 5 minutes), and suspended in PBS. With using Gene Pulser (Bio-Rad Laboratories), DNA was introduced into the cells under the conditions shown below. That is, to the cuvette of 0.4 cm gap were added $8 \times 10^6$ cells and 10 µg of plasmid pCKR5 for expression of human CCR5, and electroporation was carried out under 0.25 kV of voltage and 960 µF of capacitance.

The cells were transferred into Ham's F12 medium (Nihon Pharmaceutical) containing 10% fetal calf serum, and cultivated for 24 hours. The cells were again took off and centrifuged, and suspended in Ham's F12 medium (Nihon Pharmaceutical) containing 10% fetal calf serum and 500 µg/ml of geneticin (Life Tech Oriental). The suspension was diluted to give $10^4$ cells/ml of the suspension, which was inoculated on 96 well plate (Becton Dickinson) to give geneticin resistant cells. The resulting geneticin resistant cells were cultivated in 96 well plate (Becton Dickinson), and cells expressing CCR5 were selected from the geneticin resistant cells. That is, in assay buffer (Ham's F12 medium containing 0.5% BSA and 20 mM HEPES (Wako Pure Chemical, pH7)) to which was added 200 pM of [$^{125}$I]-RANTES (Amersham) as ligand, binding reaction was carried out at room temperature for 40 minutes, and the buffer was washed with cooled PBS. To the buffer was added 50 µl/well of 1M NaOH, and the mixture was stirred. Radioactivity was determined with γ-counter to select CHO/CCR5 cells which specifically bind to the ligand.

(4) Evaluation of Test Compounds Based on CCR5 Antagonistic Activity

The CHO/CCR5 were inoculated on 96 well microplate ($5 \times 10^4$ cells/well) and cultivated for 24 hours. The medium was removed by means of suction, and to each well was added assay buffer containing Test Compound (1 µM) and then 100 pM of [$^{125}$I]-RANTES (Amersham) as ligand.

Binding assay was carried out at room temperature for 30 minutes, and assay buffer was removed by means of suction. Each well was washed twice with cooled PBS, and 200 µl of Microscint-20 (Packard Instrument, Inc.) was added to each well. Radio-activity was determined with TopCount Micro Scintillation Counter (Packard Instrument, Inc.).

According to the method described above, inhibition rate of Test Compound (whose number is referred to in the following Examples) to CCR5 binding.

The results are shown in Table 1.

TABLE 1

| Compound Number | Inhibition Rate (%) |
|---|---|
| 1 | 99 |
| 2 | 96 |
| 3 | 96 |

(5) Inhibitory Effect on HIV-1 Infection to MAGI-CCR5 Cell

The plasmid where β-galactosidase gene was ligated downstream of HIV-1 LTR was introduced into CD4 positive HeLa cell, to which human CCR5 was further introduced to obtain transformant MAGI-CCR5. By using said transformant MAGI-CCR5, degree of HIV-1 infection was calculated from β-galactosidase activity (blue color due to decomposition of 5-bromo-4-chloro-3-indolyl-β-D-galactopyranoside). Specifically, MAGI-CCR5 cells were suspended in DMEM medium containing 10% serum to prepare $5 \times 10^4$ cells/ml suspension. To each well of 96 well plate was inoculated 200 µl of the suspension, and the cells were cultivated at 37° C. overnight. The medium was removed by means of suction, and to the residue was added 100 µl of the above medium containing 0.064 µM of Test Compound and 100 µl of the above medium containing 300 PFU of HIV-1 BA-L cells. The cells were cultivated at 37° C. for 2 days. The medium was removed by means of suction. To the residue was added 200 µl of cell fixative (PBS containing 1% formaldehyde and 0.2% glutaraldehyde), and the mixture was allowed to stand at room temperature for minutes and washed twice with PBS. To the mixture was added 100 µl of staining solution (PBS containing 4 µM potassium ferrocyanide, 4 µM potassium ferricyanade, 2 µM $MgCl_2$ and 0.4 mg/ml X-gal), and the mixture was allowed to stand at 37° C. for 50 minutes and washed twice with PBS. The number of blue cells was counted by microscope and defined as the number of cells infected with HIV-1. According to this method, inhibition rate on HIV-1 infection was determined and found that Compound No. 1 shows 100% inhibition on HIV-1 infection.

(6) Inhibitory Effect on HIV-1 Infection to Human PBMC

From normal person human peripheral blood mononuclear cells (PBMC) were separated, and the cells were stimulated with. 10 µg/ml of PHA (Phytohemaglutinin) and 20 U/ml of interleukin-2 (IL-2) for 3 days. The cells were suspended in RPMI-1640 medium containing 20% serum to prepare $1 \times 10^6$/ml suspension. To the suspension were infected HIV-1 BA-L cells (20 ng as an amount of p24 antigen), and viruses were absorbed at 37° C. for 2 hours. The cells were washed and suspended in RPMI-1640 medium containing 20% serum and IL-2 20 U/ml to prepare $1 \times 10^5$/ml suspension. To the PBMC suspension was added the same amount of a solution which contains 0.032 µM of Test Compound, and the cells were cultivated at 37° C. in carbon dioxide gas incubator. The amount of p24 antigen in supernatant of the cultivated medium was determined by enzyme-linked immunosorbent assay (ELISA) and defined as degree of HIV-1 infection. According to this method, inhibition rate on HIV-1 infection was determined and found that Compound No. 1 shows 74% inhibition on HIV-1 infection.

The pharmaceutical composition for antagonizing CCR5 (e.g. a medicament for the treatment or prevention of infectious disease of HIV, a medicament for the treatment or prevention of AIDS, etc.) comprising the compound of the formula (I) of the present invention, as an active ingredient, can be prepared, for example, by the following prescriptions:

1. Injection

A mixture of Compound 1 (500 mg), mannitol (1000 mg) and polysorbate 80 (100 mg) is dissolved in distilled water (10 ml), and to the solution is added distilled water to make the whole volume 20 ml. The solution is filtered under sterile conditions. Each 2 ml of the solution is filled into a vial for injection under sterile conditions.

Reference Example 1

To a solution of 4-nitrobenzylalcohol (50 g, 0.326 mol) in ethyl acetate (EtOAc) (200 ml) were added 3,4-dihydropyran (35.7 ml, 0.392 mol) and CSA (camphor sulfonic acid) (379 mg, 1.63 mmol) under stirring at room temperature, and the mixture was stirred at room temperature for 1 hour. After the reaction completed, the reaction mixture was neutralized with saturated $NaHCO_3$ solution and separated ethyl acetate layer was dried with $MgSO_4$ and concentrated under reduced pressure. The residue was purified with silica gel column chromatography to give 4-(2-tetrahydropyranyloxymethyl)nitrobenzene (74.5 g, 96%) as syrup.

$^1$H-NMR (200 MHz, $CDCl_3$) δ: 1.55–2.05 (6H, m), 3.51–3.62 (1H, m), 3.83–3.94 (1H, m) , 4.61 (1H, d, J=13.6 Hz), 4.74 (1H, t, J=3.2 Hz), 4.93 (1H, d, J=13.4 Hz), 7.51–7.56 (2H, d, J=8.8 Hz), 8.18–8.24 (2H, m).

Reference Example 2

To a solution of 4-(2-tetrahydropyranyloxymethyl) nitrobenzene (59.7 g, 0.256 mol) in ethanol (EtOH) (300 ml) was added under nitrogen atmosphere at room temperature 10% Pd/C (5.97 g), and catalytic hydrogenation was carried out. The mixture was stirred at room temperature for 24 hours. After the reaction completed, the catalyst was filtered off, and the organic layer was concentrated under reduced pressure. The residue was purified with silica gel column chromatography to give 4-(2-tetrahydropyranyloxymethyl) aniline (39.7 g, 76%) as syrup.

$^1$H-NMR (200 MHz, $CDCl_3$) δ: 1.45–1.95 (6H, m), 3.00–3.60 (3H, br m), 3.87–4.14 (1H, m), 4.39 (1H, d, J=11.4 Hz), 4.68 (1H, d, J=11.4 Hz), 4.71 (1H, m), 6.65–6.69 (2H, m), 7.15–7.19 (2H, m).

Reference Example 3

To a solution of 2-(4-methylphenyl)-6,7-dihydro-5H-benzocycloheptene-8-carboxylic acid (35.0 g, 0.126 mol) in tetrahydrofuran (THF) (280 ml) were added $(COCl)_2$ (21.9 ml, 0.251 mol) and DMF (0.7 ml) at 0° C. Under nitrogen atmosphere, the mixture was stirred at room temperature for 4 hours. After the reaction completed, The solvent was evaporated, and to the residue was added THF (315 ml). To a solution of the acid chloride was added a solution of 4-(2-tetrahydropyranyloxymethyl)aniline (28.1 g, 0.138 mol) and triethylamine ($Et_3N$) (26.3 ml, 0.189 mol) in THF (105 ml) at 0° C., and the mixture was stirred under nitrogen atmosphere, at room temperature for 2 hours. After the reaction completed, to the mixture was added water, and the mixture was extracted with ethyl acetate. The organic layer was washed with saturated NaCl solution and dried with $MgSO_4$. The solvent was evaporated and the residue was dissolved in methanol (MeOH) (470 ml). To the mixture was dropwise added 6N HCl (5.9 ml) at room temperature, and the mixture was stirred for 1 hour. After the reaction completed, the mixture was neutralized with saturated $NaHCO_3$ solution, and the solvent was removed. The residue was washed with water and then acetone/isopropylether (10:1; 60 ml), and the resulting precipitate was filtered, which was dissolved in THF. The mixture was dried with $MgSO_4$, and the solvent was evaporated. The resulting powder was washed twice with hexane:ethyl acetate (10:1; 50 ml) to give N-(4-hydroxymethylphenyl)-2-(4-methylphenyl)-6,7-dihydro-5H-benzocycloheptene-8-carboxamide (26.8 g, 56%) as white powder.

$^1$H-NMR (200 MHz, $CDCl_3$) δ: 2.10–2.22 (2H, m), 2.39 (3H, s), 2.71 (2H, br t, J=6.4), 2.84–2.91 (2H, m), 4.67 (2H, s), 7.20–7.26 (2H, m), 7.33–7.51 (7H, m), 7.61 (2H, d, J=8.4), 7.71 (1H, br s).

Reference Example 4

To a solution of N-(4-hydroxymethylphenyl)-2-(4-methylphenyl)-6,7-dihydro-5H-benzocycloheptene-8-carboxamide (10.0 g, 26.1 mmol) and pyridine (0.1 ml) in chloroform (150 ml) was dropwise added a solution of thionyl chloride (3.4 ml, 39.2 mmol)in chloroform (90 ml), and the mixture was stirred under nitrogen atmosphere at room temperature for 17 hours. After the reaction completed, water was added to the mixture, and the mixture was extracted with chloroform. The organic layer was washed with saturated sodium chloride solution and dried with anhydrous magnesium sulfate. The solvent was evaporated, and the resulting powder was washed with hexane to give N-(4-chloromethylphenyl)-2-(4-methylphenyl)-6,7-dihydro-5H-benzocycloheptene-8-carboxamide (10.2 g, 97%) as colorless powder.

$^1$H-NMR (200 MHz, $CDCl_3$) δ: 2.05–2.21 (2H, m), 2.40 (3H, s), 2.71 (2H, br t, J=6.4), 2.84–2.91 (2H, m), 4.58 (2H, s), 7.20–7.27 (2H, m), 7.35–7.52 (7H, m), 7.59–7.65 (2H, m), 7.71 (1H, br s). Anal. for $C_{26}H_{24}NOCl.0.25H_2O$: Calcd: C; 76.83, H; 6.08, N; 3.45. Found: C; 76.55, H; 6.00, N; 3.53.

Reference Example 5

To a solution of tetrahydro-4H-pyran-4-one (60 g, 0.6 mol) and water (5 ml) in DMF (70 ml, 0.90 mol) was added formic acid (46 ml, 1.2 mol), and the mixture was stirred at 140° C. for 23 hours. After the reaction completed, reflux apparatus was changed to evaporation apparatus, crude amine was obtained by evaporation (74.6 g).

b.p. 117–123° C. (27 mm).

To an aqueous solution (100 ml) of the crude amine (30 g) was dropwise added 6N HCl (5 drops), and the mixture was washed twice with dichloromethane. The aqueous layer was adjusted to pH 11 with sodium hydroxide. To the mixture was added NaCl, and the mixture was extracted with dichloromethane three times. The organic layer was dried with potassium carbonate, and the solvent was evaporated. The residue was purified with evaporation to give N,N-dimethyl-N-tetrahydropyran-4-ylamine (10.4 g, 29%) as colorless oil.

b.p. 75–82° C. (29 mm). $^1$H-NMR (200 MHz, $CDCl_3$) δ: 1.40–1.82 (4H, m), 2.28 (6H, s), 2.25–2.40 (1H, m), 3.37 (2H, ddd, J=11.8, 11.8 and 2.2), 3.97–4.05 (2H, m).

Reference Example 6

To a suspension of 7-(4-methylphenyl)-2,3-dihydro-1-benzoxepine-4-carboxylic acid (0.6 g, 2.1 mmol) in tetrahydrofuran (10 ml) were added oxalyl chloride (0.33 ml, 4.3 mmol) and N,N-dimethylformamide (1 drop) at 0° C., and the mixture was stirred at room temperature for 2.5 hours. The solvent was evaporated, and the residue was dissolved in tetrahydrofuran (6 ml). To the mixture was dropwise added 4-(t-butyldimethylsilyloxymethyl)aniline (0.56 g, 2.4 mmol) and triethylamine (0.36 ml, 2.6 mmol) in tetrahydrofuran (2 ml) at 0° C., and the mixture was stirred at room temperature for 16 hours. To the reaction mixture was added water, and the mixture was extracted with ethyl acetate. The extract was washed with saturated sodium chloride solution and dried with magnesium sulfate. The solvent was evaporated, and the residue was subjected to silica gel column chromatography. Crude amide (1.1 g) was obtained from fractions of hexane:ethyl acetate=5:1. This product was dissolved in acetone (8 ml), and to the mixture was dropwise added 6N hydrochloric acid. The mixture was stirred for 1 hour. To the mixture were added 1% sodium hydrogen carbonate (100 ml) and diisopropylether (100 ml), and precipitate was filtered, which were dissolved in acetone. The mixture was dried with magnesium sulfate, and the solvent was evaporated. The resulting powder was recrystallized from acetone-diisopropyl-ether to give N-(4-hydroxymethylphenyl)-7-(4-methylphenyl)-2,3-dihydro-1-benzoxepine-4-carboxamide (0.87 g) as colorless crystals.

$^1$H-NMR (CDCl$_3$) δ: 2.39 (3H, s), 3.08 (2H, br t, J=4.4), 4.36 (2H, t, J=4.4), 4.68 (2H, s), 7.06 (2H, d, J=8.4), 7.18–7.61 (10H, m), 7.24 (2H, d, J=8.4). Anal. for C$_{25}$H$_{23}$NO$_3$: Calcd: C; 77.90, H; 6.01, N; 3.63. Found: C; 77.91, H; 6.10, N; 3.55.

Reference Example 7

To a solution of N-(4-hydroxymethylphenyl)-7-(4-methylphenyl)-2,3-dihydro-1-benzoxepine-4-carboxamide (412 mg, 1.07 mmol) and pyridine (1 drop) in chloroform (5 ml) was dropwise added thionyl chloride (0.14 ml, 1.61 mmol), and the mixture was stirred for 2 hours. The mixture was diluted with water and extracted with chloroform. The extract was washed with saturated sodium chloride solution and dried with magnesium sulfate. The solvent was evaporated, and the resulting powder was washed with hexane-ethyl acetate (1:1) to give N-(4-chloromethylphenyl)-7-(4-methylphenyl)-2,3-dihydro-1-benzoxepine-4-carboxamide (380 mg, 88%) as colorless powder.

m.p. 164° C. $^1$H-NMR (CDCl$_3$) δ: 3.29 (3H, s), 3.07 (2H, t, J=4.8), 4.36 (2H, t, J=4.8), 4.59 (2H, s), 7.05 (1H, d, J=8.2), 7.22–7.26 (2H, m), 7.36–7.52 (6H, m), 7.57–7.62 (3H, m). Anal. for C$_{25}$H$_{22}$NO$_2$Cl: Calcd: C; 74.34, H; 5.49, N; 3.47. Found: C; 74.00, H; 5.42, N; 3.29.

Reference Example 8

To a suspension of 1,4-cyclohexanedione monoethyleneketal (3.82 g, 24.6 mmol) and dimethylamine hydrochloride (2.00 g, 24.6 mmol) in 1,2-dichloroethane (50 ml) were dropwise added triethylamine (4.2 ml, 29.6 mmol) and DBU (1,8-diazabicyclo-[5.4.0]-7-undecene) (4.4 ml), and the mixture was stirred for 10 minutes. To the mixture was added triacetoxyborohydride (7.68 g, 34.4 mmol), and the mixture was stirred for 4.5 hours. Precipitate was filtered off, and the filtrate was concentrated to give crude product (6.34 g), which was dissolved in water (10 ml). To the mixture was dropwise added concentrated hydrochloric acid (6 ml), and the mixture was stirred for 48 hours. The reaction mixture was diluted with water and washed twice with ether. The aqueous layer was made basic with sodium hydroxide and extracted with ether twice. The extract was washed with saturated sodium chloride solution, dried with potassium carbonate and purified by evaporation to give 4-dimethylaminocyclohexanone (0.59 g, 17%).

b.p.142–145° C. $^1$H-NMR (CDCl$_3$) δ: 1.69–2.13 (4H, m), 2.32 (6H, s), 2.20–2.41 (2H, m), 2.44–2.64 (3H, m).

Reference Example 9

To a solution of 7-(4-ethoxyphenyl)-2,3-dihydro-1-benzoxepine-4-carboxylic acid (2.38 g) in THF (50 ml) were added oxalyl chloride (1.4 ml) and DMF (2 drops) at room temperature, and the mixture was stirred for 1 hour. Under reduced pressure, the solvent was evaporated, and the residue was dissolved in THF (50 ml). To the mixture was dropwise added a solution of triethylamine (2.1 ml) and 4-aminobenzyloxy-tert-butyldimethylsilane (2.00 g) in THF (10 ml) at 0° C., and the mixture was stirred at room temperature for 18 hours. To the reaction mixture was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:4) to give pale yellow crystals (3.99 g), which were dissolved in acetone (50 ml). To the mixture was added 6N hydrochloric acid (1.3 ml) at room temperature, and the mixture was stirred for 1 hour. To the reaction mixture were added 5% sodium hydrogen carbonate solution (15 ml) and diisopropylether (100 ml). Precipitate was collected by filtration and washed with water and diisopropylether. The resulting solid was dissolved in THF, dried with magnesium sulfate and concentrated under reduced pressure to give crystals, which were recrystallized from THF to give 7-(4-ethoxyphenyl)-N-(4-hydroxymethylphenyl)-2,3-dihydro-1-benzoxepine-4-carboxamide (2.65 g) as colorless crystals.

m.p. 208–210° C. $^1$H-NMR (200 MHz, DMSO-d$_6$) δ: 1.35 (3H, t, J=7.0 Hz), 2.93–3.03 (2H, m), 4.06 (2H, q, J=7.0 Hz), 4.45 (2H, br s), 5.01–5.18 (1H, m), 6.98–7.05 (3H, m), 7.25–7.34 (3H, m), 7.49–7.71 (6H, m), 9.92 (1H, s). IR (KBr) ν: 3363, 3290, 1659, 1612, 1525, 1493, 1242, 1227, 825 cm$^{-1}$ Anal. for C$_{26}$H$_{25}$NO$_4$ Calcd: C, 75.16 ; H, 6.06 ; N, 3.37 Found: C, 75.16 ; H, 6.08 ; N, 3.31.

Reference Example 10

To a suspension of 7-(4-ethoxyphenyl)-N-(4-hydroxymethylphenyl)-2,3-dihydro-1-benzoxepine-4-carboxamide (2.55 g) and pyridine (2 drops) in chloroform (50 ml) was added thionyl chloride (0.8 ml) at room temperature, and the mixture was stirred for 20 hours. To the reaction mixture was added water and then THF, and the mixture was extracted with ethyl acetate. The organic layer was washed with saturated sodium chloride solution, dried with magnesium sulfate and concentrated under reduced pressure to give solid, which was dissolved in THF and ethyl acetate. The mixture was concentrated under reduced pressure to give crystals, which were collected by filtration and washed with diisopropylether to give N-(4-chloromethylphenyl)-7-(4-ethoxyphenyl)-2,3-dihydro-1-benzoxepine-4-carboxamide (2.42 g) as colorless crystals.

m.p. 187–189° C. $^1$H-NMR (200 MHz, DMSO-d$_6$) δ: 1.35 (3H, t, J=7.0 Hz), 2.93–3.04 (2H, m), 4.06 (2H, q, J=7.0 Hz), 4.23–4.34 (2H, m), 4.74 (2H, s), 6.98–7.06 (3H, m), 7.35–7.42 (3H, m), 7.52 (1H, dd, J=8.4; 2.2 Hz), 7.59 (2H, d, J=8.8 Hz), 7.70–7.74 (3H, m), 10.04 (1H, s). IR (KBr) ν: 3400, 1659, 1610, 1525, 1493, 1242, 1047, 822 cm$^{-1}$ Anal. for $C_{26}H_{24}NO_3Cl$ Calcd: C, 71.97 ; H, 5.57 ; N, 3.23 Found: C, 71.96 ; H, 5.54 ; N, 3.04.

Reference Example 11

To solution of 7-(4-ethoxyphenyl)-N-[4-[N-methyl-N-(tetrahydropyran-4-yl)aminomethyl]phenyl]-2,3-dihydro-1-benzoxepine-4-carboxamide (111 mg) in DMF (5 ml) was added methyl iodide (0.04 ml) at room temperature, and the mixture was stirred for 8 hours. Under reduced pressure, the mixture was concentrated, and to the residue was added ethyl acetate to precipitate solid, which was collected by filtration and recrystallized from ethanol-ethyl acetate to give dimethyl-[4-N-[7-(4-ethoxyphenyl)-2,3-dihydro-1-benzoxepin-4-carbonyl]aminobenzyl]-4-tetrahydropyranylammonium iodide (97 mg) as pale yellow crystals.

m.p. 152–158° C. $^1$H-NMR (200 MHz, CDCl$_3$) δ: 1.41 (3H, t, J=7.0 Hz), 1.68–1.98 (2H, m), 2.10–2.26 (2H, m), 2.94 (6H, s), 2.98–3.08 (2H, m), 3.35–3.59 (3H, m), 3.96–4.16 (2H, m), 4.03 (2H, q, J=7.0 Hz), 4.19–4.31 (2H, m), 4.84 (2H, s), 6.91 (2H, d, J=8.8 Hz), 6.97 (1H, d, J=8.4 Hz), 7.38 (1H, dd, J=8.4, 2.2 Hz), 7.44–7.57 (5H, m), 7.69 (1H, d, J=2.2 Hz), 7.80 (2H, d, J=8.4 Hz), 8.01 (1H, s). IR (KBr) ν: 3440, 1657, 1605, 1520, 1491, 1317, 1240 cm$^{-1}$ Anal. for $C_{33}H_{39}N_2O_4I.1.0H_2O$ Calcd: C, 58.93; H, 6.14; N, 4.16 Found: C, 58.86; H, 6.18; N, 4.19.

Reference Example 12

To a solution of 7-(4-ethylphenyl)-N-[4-[N-methyl-N-(tetrahydropyran-4-yl)aminomethyl]phenyl]-2,3-dihydro-1-benzoxepine-4-carboxamide (125 mg) in DMF (5 ml) was added methyl iodide (0.04 ml) at room temperature, and the mixture was stirred for 20 hours. Under reduced pressure, the mixture was concentrated, and to the residue was added ethyl acetate to precipitate solid, which was collected by filtration and recrystallized from acetone-diethylether→ethanol-diethylether) to give dimethyl-[4-N-[7-(4-ethylphenyl)-2,3-dihydro-1-benzoxepin-4 -carbonyl] aminobenzyl]-4-tetrahydropyranylammonium iodide (68 mg) as pale yellow crystals.

m.p. 156–160° C. $^1$H-NMR (200 MHz, CDCl$_3$) δ: 1.25 (3H, t, J=7.6 Hz), 1.69–1.93 (2H, m), 2.13–2.28 (2H, m), 2.66 (2H, q, J=7.6 Hz), 2.95 (6H, s), 3.00–3.09 (2H, m), 3.39–3.56 (2H, m), 4.02–4.34 (5H, m), 4.86 (2H, s), 6.99 (1H, d, J=8.4 Hz), 7.18–7.28 (3H, m), 7.39–7.56 (5H, m), 7.69–7.73 (1H, m), 7.79 (2H, d, J=8.8 Hz), 8.78 (1H, s). IR (KBr) ν: 3429, 1657, 1301, 1520, 1491, 1412, 1319, 1244, 827 cm$^{-1}$ Anal. for $C_{33}H_{39}N_2O_3I.1.0H_2O$ Calcd: C, 60.37 ; H, 6.29 ; N, 4.27 Found: C, 60.40 ; H, 6.24 ; N, 4.10.

Reference Example 13

To a solution of N-[4-[N-methyl-N-(tetrahydropyran-4-yl)aminomethyl]phenyl]-7-(4-trifluoromethylphenyl)-2,3-dihydro-1-benzoxepine-4-carboxamide (113.6 mg) in DMF (5 ml) was added methyl iodide (0.04 ml) at room temperature, and the mixture was stirred for 24 hours. Under reduced pressure, the mixture was concentrated, and to the residue was added ethyl acetate to precipitate solid, which was collected by filtration and recrystallized from acetone-diethylether→ethanol-diethyl-ether) to give dimethyl-[4-N-[7-(4-trifluoromethylphenyl)-2,3-dihydro-1-benzoxepin-4-carbonyl]aminobenzyl]-4-tetrahydropyranylammonium iodide (99 mg) as pale yellow crystals.

m.p. 213° C. (dec.) $^1$H-NMR (200 MHz, DMSO-d$_6$) δ: 1.42–1.66 (2H, m), 1.75–1.88 (2H, m), 2.55 (6H, s), 2.62–2.72 (2H, m), 2.94–3.35 (3H, m), 3.68–3.81 (2H, m), 3.96–4.08 (2H, m), 4.13 (2H, s), 6.80 (1H, d, J=8.8 Hz), 7.05 (1H, s), 7.21 (2H, d, J=8.4 Hz), 7.34–7.40 (1H, m), 7.44–7.63 (7H, m), 9.89 (1H, s). IR (KBr) ν: 3277, 1649, 1510, 1520, 1491, 1325, 1255, 1120, 843 cm$^{-1}$ Anal. for $C_{32}H_{34}N_2O_3F_3I.0.2H_2O$ Calcd: C, 56.35 ; H, 5.08 ; N, 4.11 Found: C, 56.21 ; H, 5.16 ; N, 4.11.

Reference Example 14

In 1,2-dichloroethane(400 ml) was suspended p-nitrobenzylamine hydrochloride (30.8 g), 1,4-cyclohexane-dione monoethyleneketal (25.4 g) and triethylamine (23 ml), and to the suspension was added sodium triacetoxy boron hydride (50.9 g) under ice-cooling. Under nitrogen atmosphere, the mixture was stirred at room temperature for 2.5 hours. Under ice-cooling , 37% formalin (14.6 ml) and sodium triacetoxy boron hydride (50.9 g) were added to the mixture. Under nitrogen atmosphere, the mixture was stirred at room temperature overnight. The mixture was neutralized with sodium hydrogen carbonate and extracted with 1,2-dichloroethane. The organic layer was washed with sodium chloride solution and dried with anhydrous magnesium sulfate. Under reduced pressure, the solvent was evaporated to give yellow solid (47.5 g), 44 g of which was dissolved in (660 ml). To the mixture was added reduced iron (32 g) little by little, and the mixture was stirred at room temperature overnight. The solvent was evaporated, and to the residue was added ethyl acetate. The precipitate was filtered off, and the filtrate was made alkaline with potassium carbonate and extracted with ethyl acetate. The organic layer was washed with water and saturated sodium chloride solution and dried with anhydrous magnesium sulfate. Under reduced pressure, the solvent was evaporated, and the residue was purified with silica gel column chromatography (ethyl acetate/triethylamine/methanol) to give 4-((N-(4,4-ethylenedioxycyclohexyl)-N-methyl) aminomethyl)aniline (34.1 g) as brown oil.

$^1$H-NMR(CDCl$_3$) δ: 1.36–1.93 (8H, m), 2.17 (3H, s), 2.43–2.57 (1H, m), 3.46 (2H, s), 3.60 (2H, br), 3.94 (4H, s), 6.64 (2H, d, J=8.4 Hz), 7.09 (2H, d, J=8.4 Hz). IR(neat) ν: 2946, 1615 cm$^{-1}$.

Reference Example 15

In dichloromethane (400 ml) was suspended 7-(4-methylphenyl)-2,3-dihydro-1-benzoxepine-4-carboxylic acid (17.0 g), and to the suspension were added oxalyl chloride (10.3 ml) and dimethylformamide (catalytic amount) under ice-cooling. The mixture was stirred at room temperature for 2 hours, and the solvent was evaporated. The residue was dissolved in tetrahydrofuran (300 ml), and the mixture was dropwise added to a solution of 4-((N-(4,4-ethylenedioxycyclohexyl)-N-methyl)aminomethyl)-aniline (16.75 g) and triethylamine (25 ml) in tetrahydrofuran (200 ml), under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate to give N-(4-((N-(4,4-ethylenedioxycyclohexyl)-N-methyl) aminomethyl)phenyl)-7-(4-methylphenyl)-2,3-dihydro-1-benzoxepine-4-carboxamide (17.1 g) as colorless crystals.

mp 192–193° C. $^1$H-NMR(CDCl$_3$) δ: 1.48–1.86 (8H, m), 2.20 (3H, s), 2.39 (3H, s), 2.45–2.60 (1H, m), 3.08 (2H, t, J=4.5 Hz), 3.56 (2H, s), 3.95 (4H, s), 4.36 (2H, t, J=4.5 Hz), 7.06 (1H, d, J=8.4 Hz), 7.23–7.33 (4H, m), 7.44–7.56 (7H, m). IR(KBr) ν: 2948, 1651 cm$^{-1}$. Anal. for C$_{34}$H$_{38}$N$_2$O$_4$: Calcd: C, 75.81; H, 7.11; N, 5.20. Found: C, 75.51; H, 6.99; N, 5.29.

Reference Example 16

In acetic acid (100 ml) and 1N hydrochloric acid (200 ml) was dissolved N-(4-((N-(4,4-ethylenedioxycyclohexyl)-N-methyl)aminomethyl)phenyl)-7-(4-methylphenyl)-2,3-dihydro-1-benzoxepine-4-carboxamide (17.1 g), and the mixture was stirred at 100° C. for 1.5 hours and concentrated. The residue was neutralized with 1N sodium hydroxide and extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate-methanol to give N-(4-((N-(4-oxocyclohexyl)-N-methyl) aminomethyl)phenyl)-7-(4-methylphenyl)-2,3-dihydro-1-benzoxepine-4-carboxamide (12 g) as colorless crystals.

mp 149–150° C. $^1$H-NMR(CDCl$_3$) δ: 1.78–2.13 (4H, m), 2.23 (3H, s), 2.25–2.35 (2H, m), 2.39 (3H, s), 2.45–2.57 (2H, m), 2.84–2.94 (1H, m), 3.08 (2H, t, J=4.4 Hz), 3.59 (2H, s), 4.35 (2H, t, J=4.4 Hz), 7.06 (1H, d, J=8.0 Hz), 7.22–7.34 (4H, m), 7.43–7.57 (6H, m), 7.65 (1H, s). IR(KBr) ν: 2946, 1713cm$^{-1}$. Anal. for C$_{32}$H$_{34}$N$_2$O$_3$ Calcd: C, 77.70; H, 6.93; N, 5.66. Found: C, 77.45; H, 6.78; N, 5.65.

Reference Example 17

To a mixture of methyl 2-bromo-6,7-dihydro-5H-benzocycloheptene-8-carboxylate (0.5 g), 4-(1-pyrrolidinyl) phenyl borate(0.37 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.08 g), and the mixture was refluxed for 6 hours and extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/ hexane) to give colorless crystals (0.48 g), which were dissolved in 1N sodium hydroxide (15 ml), methanol (50 ml) and tetrahydrofuran (50 ml). The mixture was stirred at room temperature overnight, concentrated and neutralized with hydrochloric acid to precipitate 2-(4-(1-pyrrolidinyl) phenyl)-6,7-dihydro-5H-benzocycloheptene-8-carboxylic acid (0.46 g) as pale yellow crystals.

mp 242–243° C.(dec.). $^1$H-NMR(DMSO-d$_6$) δ: 1.93–2.00 (6H ,m), 2.56 (2H, t, J=5.8 Hz), 2.76–2.82 (2H, m), 3.23–3.35 (4H, m), 6.60 (2H, d, J=8.8 Hz), 7.20 (1H, d, J=8.2 Hz), 7.44 (1H, dd, J=1.0, 8.2 Hz), 7.53 (2H, d, J=8.8 Hz), 7.56 (1H, d, J=1.0 Hz), 7.69 (1H, s). Anal. for C$_{22}$H$_{23}$NO$_2$.0.1H$_2$O: Calcd: C, 78.82; H, 6.98; N, 4.18. Found: C, 78.92; H, 6.95; N, 4.15.

Reference Example 18

To a solution of 2-(4-(1-pyrrolidinyl)phenyl)-6,7-dihydro-5H-benzocycloheptene-8-carboxylic acid (0.45 g), 4-(N-methyl-N-(tetrahydropyran-4-yl)aminomethyl)aniline (0.33 g) and 1-hydroxybenzotriazole (0.18 g) in dimethylformamide (20 ml) was added 1-ethyl-3-(3-dimethylaminopropyl)carbodiimide hydrochloride (0.39 g) under ice-cooling. Under nitrogen atmosphere, the reaction mixture was cooled to room temperature, and to the mixture were added 4-dimethylaminopyridine (catalytic amount) and triethylamine (0.56 ml). The mixture was stirred overnight, poured into water and extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give 2-(4-(1-pyrrolidinyl)phenyl)-N-(4-((N-tetrahydropyran-4-yl-N-methyl)aminomethyl)phenyl)-6,7-dihydro-5H-benzocycloheptene-8-carboxamide (0.28 g) as colorless crystals.

mp 124–125° C. $^1$H-NMR(CDCl$_3$)δ: 1.66–1.77 (4H, m), 1.99–2.06 (4H, m), 2.11–2.18 (2H, m), 2.21 (3H, s), 2.55–2.75 (3H, m), 2.84–2.90 (2H, m), 3.30–3.44 (6H, m), 3.58 (2H, s), 4.00–4.14 (2H, m), 6.64 (2H, d, J=9.0 Hz), 7.19 (1H, d, J=8.0 Hz), 7.31 (2H, d, J=8.5 Hz), 7.39–7.51 (4H, m), 7.57 (2H, d, J=8.5 Hz), 7.64 (1H, s). IR(KBr) ν: 2946, 2843, 1651, 1611 cm$^{-1}$. Anal. for C$_{35}$H$_{41}$N$_3$O$_2$.0.2H$_2$O Calcd: C, 77.95; H, 7.74; N, 7.79. Found: C, 77.76; H, 7.59; N, 7.79.

Reference Example 19

In 1,2-dichloroethane (50 ml) were dissolved p-nitrobenzaldehyde (5 g) and 3-amino-1-propanol (2.5 g), and to the mixture was added sodium triacetoxy boron hydride (9.8 g) under ice-cooling. Under nitrogen atmosphere, the mixture was stirred at room temperature for 5 hours. Under ice-cooling, to the mixture was added 37% formalin (3 ml) and sodium triacetoxy boron hydride (9.8 g). Under nitrogen atmosphere, the mixture was stirred at room temperature overnight. To the mixture was added water, and the mixture was concentrated, neutralized with aqueous sodium hydroxide and extracted with ethyl acetate. The organic layer was washed with water and sodium chloride solution and dried with anhydrous magnesium sulfate. Under reduced pressure, the solvent was evaporated, and the residue was purified with silica gel column (ethyl acetate/ methanol/triethylamine) to give yellow oil (5.0 g), 2.5 g of which was dissolved in ethanol (50 ml) and catalytic hydrogenation was carried out with 5% palladium on carbon (0.2 g) for 1.5 hours. The catalyst was filtered off, and the solvent was evaporated. The residue was purified with silica gel column (ethyl acetate/methanol/triethylamine) to give 4-((N-3-hydroxypropyl-N-methyl)aminomethyl)-aniline (1.5 g) as pale yellow oil.

$^1$H-NMR(CDCl$_3$) δ: 1.67–1.78 (2H, m), 2.21 (3H, s), 2.62 (2H, t, J=5.5 Hz), 3.41 (2H, s), 3.65 (2H, br), 3.77 (2H, t, J=5.1 Hz), 6.65 (2H, d, J=8.4 Hz), 7.07 (2H, d, J=8.4 Hz). IR (neat) ν: 3347, 2948, 2799, 1615 cm$^{-1}$.

Reference Example 20

In dichloromethane (5 ml) was suspended 2-(4-methylphenyl)-6,7-dihydro-5H-benzocycloheptene-8-carboxylic acid (0.3 g), and to the suspension were added oxalyl chloride (0.28 ml) and dimethylformamide (catalytic amount) under ice-cooling. The mixture was stirred at room temperature for 1.5 hours, and the solvent was evaporated. The residue was dissolved in tetrahydrofuran (15 ml), and the mixture was dropwise added to a solution of 4-((N-3-hydroxypropyl-N-methyl)aminomethyl)aniline (0.23 g) and triethylamine (0.45 ml) in tetrahydrofuran (15 ml) under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-((N-3-hydroxypropyl-N-methyl)aminomethyl)phenyl)-2-(4-methylphenyl)-6,7-dihydro-5H-benzocycloheptene-8-carboxamide (0.32 g) as colorless crystals.

mp 139–140° C. $^1$H-NMR (CDCl$_3$) δ: 1.72–1.81 (2H, m), 2.13–2.19 (2H, m), 2.25 (3H, s), 2.40 (3H, s), 2.63–2.75 (4H, m), 2.86–2.92 (2H, m), 3.53 (2H, s), 3.79 (2H, t, J=5.4 Hz), 7.21–7.32 (3H, m), 7.42–7.52 (6H, m), 7.58 (2H, d, J=8.4 Hz), 7.66 (1H, s). IR(KBr) ν: 2936, 1651 cm$^{-1}$. Anal. for C$_{30}$H$_{34}$N$_2$O$_2$.0.5H$_2$O: Calcd: C, 77.72; H, 7.61; N, 6.04. Found: C, 77.94; H, 7.62; N, 6.15.

Reference Example 21

In dichloromethane (12 ml) was suspended 7-(4-methylphenyl)-2,3-dihydro-1-benzoxepine-4-carboxylic acid (0.4 g), and to the suspension were added oxalyl chloride (0.37 ml) and dimethylformamide (catalytic amount) under ice-cooling. The mixture was stirred at room temperature for 2 hours, and the solvent was evaporated. The residue was dissolved in tetrahydrofuran (15 ml), and the mixture was dropwise added to a solution of 4-((N-3-hydroxy-propyl-N-methyl)aminomethyl)aniline (0.33 g) and tri-ethylamine (0.6 ml) in tetrahydrofuran (15 ml) under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-((N-3-hydroxypropyl-N-methyl)aminomethyl)phenyl)-7-(4-methylphenyl)-2,3-dihydro-1-benzoxepine-4-carboxamide (0.39 g) as colorless crystals.

mp 119–120° C. $^1$H-NMR(CDCl$_3$) δ: 1.68–1.80 (2H, m), 2.24 (3H, s), 2.39 (3H, s), 2.65 (2H, t, J=5.8 Hz), 3.07 (2H, t, J=4.6 Hz), 3.52 (2H, s), 3.77 (2H, t, J=5.2 Hz), 4.35 (2H, t, J=4.6 Hz), 7.05 (1H, d, J=8.4 Hz), 7.22–7.31 (3H, m), 7.43–7.52 (5H, m), 7.57 (2H, d, J=8.4 Hz), 7.78 (1H, s). IR (KBr) ν: 3287, 2948, 1649 cm$^{-1}$. Anal. for C$_{29}$H$_{32}$N$_2$O$_3$.0.2H$_2$O: Calcd: C, 75.69; H, 7.10; N, 6.09. Found: C, 75.58; H, 6.93; N, 6.08.

Reference Example 22

In dichloromethane (10 ml) was suspended 7-(4-methylphenyl)-2,3-dihydro-1-benzothiepine-4-carboxylic acid (0.3 g), and to the suspension were added oxalyl chloride (0.27 ml) and dimethylformamide (catalytic amount) under ice-cooling. The mixture was stirred at room temperature for 2 hours, and the solvent was evaporated. The residue was dissolved in tetrahydrofuran (15 ml), and the mixture was dropwise added to a solution of 4-(N-methyl-N-(tetrahydropyran-4-yl)aminomethyl)aniline (0.25 g) and triethylamine (0.42 ml) in tetrahydrofuran (15 ml) under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate-hexane to give 7-(4-methylphenyl)-N-(4-((N-tetrahydropyran-4-yl-N-methyl)aminomethyl)phenyl)-2,3-dihydro-1-benzothiepine-4-carboxamide (0.45 g) as colorless crystals.

mp 177–178° C. $^1$H-NMR (CDCl$_3$) δ: 1.63–1.77 (4H, m), 2.21 (3H, s), 2.40 (3H, s), 2.57–2.70 (1H, m), 3.08 (2H, t, J=5.8 Hz), 3.26–3.44 (4H, m), 3.57 (2H, s), 4.01–4.11 (2H, m), 7.24–7.34 (3H, m), 7.40–7.57 (8H, m), 7.70 (1H, s). IR (KBr) ν: 2949, 1651 cm$^{-1}$. Anal. for C$_{31}$H$_{34}$N$_2$O$_2$S.0.3H$_2$O: Calcd: C, 73.86; H, 6.92; N, 5.56. Found: C, 73.93; H, 6.73; N, 5.82.

Reference Example 23

In dichloromethane (6 ml) was suspended 2-(4-methylphenyl)-6,7-dihydro-5H-benzocycloheptene-8-carboxylic acid (0.25 g), and to the suspension were added oxalyl chloride (0.24 ml) and dimethylformamide (catalytic amount) under ice-cooling. The mixture was stirred at room temperature for 1.5 hours, and the solvent was evaporated. The residue was dissolved in tetrahydrofuran (15 ml, and the mixture was dropwise added to a solution of 4-((N-methyl-N-(pentan-3-yl))aminomethyl)aniline (0.2 g) and triethylamine (0.38 ml) in tetrahydrofuran (15 ml) under ice-cooling. Under nitrogen atmosphere, the mixture was stirred at room temperature for 5 hours, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate-hexane to give N-(4-((N-methyl-N-(pentan-3-yl))aminomethyl)phenyl)-2-(4-methylphenyl)-6,7-dihydro-5H-benzocycloheptene-8-carboxamide (0.23 g) as colorless crystals.

mp 112–113° C. $^1$H-NMR(CDCl$_3$) δ: 0.94 (6H, t, J=7.3 Hz), 1.26–1.54 (4H, m), 2.14 (3H, s), 2.14–2.32 (3H, m), 2.40 (3H, s), 2.72 (2H, t, J=6.4 Hz), 2.86–2.91 (2H, m), 3.55 (2H, s), 7.21–7.27 (3H, m), 7.31–7.56 (8H, m), 7.62 (1H, s). IR (KBr) ν: 2930, 1651 cm$^{-1}$. Anal. for C$_{32}$H$_{38}$N$_2$O: Calcd: C, 82.36; H, 8.21; N, 6.00. Found: C, 82.30; H, 8.05; N, 5.90.

Reference Example 24

To a mixture of 3-(4-methylphenyl)-6,7,8,9-tetra-hydro-5H-benzocycloheptan-5-one (0.5 g), potassium carbonate (1.65 g) and 18-crown-6 (1.05 g) was added dimethylsulfoxide (10 ml). Under carbon dioxide atmosphere, the mixture was stirred at room temperature for 20 hours, poured into water, acidified with hydrochloric acid and extracted with ethyl acetate. The organic layer was washed with water and subjected to back extraction with sodium hydroxide and water. The aqueous layer was collected, acidified with hydrochloric acid and extracted with ethyl acetate. The organic layer was washed with water and saturated sodium chloride solution and dried with anhydrous magnesium sulfate. The solvent was evaporated to precipitate colorless crystals (0.42 g), which were filtered with hexane and dissolved in ethanol (40 ml). To the mixture was added sodium boron hydride (0.54 g), and the mixture was stirred at room temperature for 1 hour. To the mixture was added water, and the mixture was concentrated, was acidified with hydrochloric acid and extracted with ethyl acetate. The organic layer was washed with water and saturated sodium chloride solution and dried with anhydrous magnesium sulfate. The solvent was evaporated to give colorless crystals (0.41 g), which were dissolved in 80% formic acid (40 ml). The mixture was stirred at 100° C. for 2.5 hours and concentrated. To the residue was added water, and the mixture was extracted with ethyl acetate. The organic layer was washed with water and saturated sodium chloride solution and dried with anhydrous magnesium sulfate. The solvent was evaporated, and the residue was purified with silica gel column (ethyl acetate/hexane) to give 2-(4-methylphenyl)-6,7-dihydro-5H-benzocycloheptene-8-carboxylic acid (0.14 g) as colorless crystals.

$^1$H-NMR (CDCl$_3$)δ: 2.04–2.18 (2H, m), 2.40 (3H, s), 2.70 (2H, t, J=6.8 Hz), 2.86–2.91 (2H, m), 7.21–7.28 (3H, m), 7.44–7.56 (4H, m), 7.91 (1H, s).

Reference Example 25

In dimethylsulfoxide (15 ml) were dissolved 3-(4-methylphenyl)-6,7,8,9-tetrahydro-5H-benzocycloheptan-5-one (0.5 g) and 18-crown-6 (1.05 g). Under ice-cooling, potassium t-butoxide (1.65 g) was added to the solution. Under carbon dioxide atmosphere, the mixture was stirred at room temperature for 3 hours, poured into water, acidified with hydrochloric acid and extracted with ethyl acetate. The organic layer was washed with water and subjected to back extraction with sodium hydroxide and water. The aqueous layer was collected, acidified with hydrochloric acid and extracted with ethyl acetate. The organic layer was washed with water and saturated sodium chloride solution and dried with anhydrous magnesium sulfate. The solvent was evaporated to precipitate colorless crystals (0.47 g), which were filtered with hexane and dissolved in ethanol (40 ml). To the mixture was added sodium boron hydride (0.58 g), and the mixture was stirred at room temperature for 1 hour. To the mixture was added water, and the mixture was concentrated, acidified with hydrochloric acid and extracted with ethyl acetate. The organic layer was washed with water and saturated sodium chloride solution and dried with anhydrous magnesium sulfate. The solvent was evaporated to precipitate colorless crystals (0.46 g), which were filtered with hexane. To the crystals was added 80% formic acid (10 ml), and the mixture was refluxed for 1.5 hours. To the mixture was added water, and the mixture was extracted with ethyl acetate. The organic layer was washed with water and subjected to back extraction with sodium hydroxide and water. The aqueous layer was collected, acidified with hydrochloric acid and extracted with ethyl acetate. The organic layer was washed with water and saturated sodium chloride solution and dried with anhydrous magnesium sulfate. The solvent was evaporated to precipitate 2-(4-methylphenyl)-6,7-dihydro-5H-benzocycloheptene-8-carboxylic acid (0.22 g) as colorless crystals.

$^1$H-NMR (CDCl$_3$) δ: 2.04–2.16 (2H, m), 2.40 (3H, s), 2.69 (2H, t, J=6.7 Hz), 2.86–2.91 (2H, m), 7.21–7.278 (3H, m), 7.44–7.56 (4H, m), 7.89 (1H, s).

Reference Example 26

In dimethylformamide (100 ml) was dissolved 7-(4-methylphenyl)-N-(4-((N-(4-oxocyclohexyl)-N-methyl)-aminomethyl)-phenyl)-2,3-dihydro-1-benzoxepin-4-carboxamide (7.5 g), and to the mixture was added methyl iodide (4.7 ml). Under nitrogen atmosphere, the mixture was stirred at room temperature overnight. The solvent was evaporated, and to the residue was added acetone to give dimethyl-(N-(7-(4-methylphenyl)-2,3-dihydro-1-benzoxepin-4-carbonyl)-4-aminobenzyl)-N-(4-oxocyclohexyl)ammonium iodide (8.9 g) as colorless crystals.

$^1$H-NMR(DMSO-d$_6$) δ: 2.09–2.24 (2H, m), 2.34 (3H, s), 2.41–2.61 (6H, m), 2.97 (6H, s), 2.97–3.00 (2H, m), 3.79–3.90 (1H, m), 4.31 (2H, t, J=4.4 Hz), 4.56 (2H, s), 7.07 (1H, d, J=8.4 Hz), 7.27 (2H, d, J=8.2 Hz), 7.37 (1H, s), 7.55–7.60 (5H, m), 7.75 (1H, d, J=2.2 Hz), 7.88 (2H, d, J=8.8 Hz), 10.20 (1H, s).

Reference Example 27

In dimethylformamide (5 ml) was dissolved in 2-(4-(1-pyrrolidinyl)phenyl)-N-(4-((N-tetrahydropyran-4-yl-N-methyl)aminomethyl)phenyl)-6,7-dihydro-5H-benzocycloheptene-8-carboxamide (0.15 g), and to the mixture was added methyl iodide (0.02 ml). Under nitrogen atmosphere, the mixture was stirred at room temperature overnight. To the mixture was added ethyl acetate, and crude crystal was filtered. The crude crystal was recrystallized from ethanol-ethyl acetate to give dimethyl-(N-(2-(4-(1-pyrrolidinyl)phenyl)-6,7-dihydro-5H-benzocycloheptene-8-carbonyl)-4-aminobenzyl)-4-tetrahydropyranylammonium iodide (0.05 g) as pale brown powder.

$^1$H-NMR(DMSO-d$_6$) δ: 1.80–2.20 (10H, m) , 2.63 (2H, t, J=5.6 Hz), 2.81–2.84 (2H, m), 2.88 (6H, s), 3.24–3.44 (6H, m), 3.54–3.65 (1H, m), 4.02–4.11 (2H, m), 4.46 (2H, s), 6.62 (2H, d, J=9.0 Hz), 7.25 (1H, d, J=7.8 Hz), 7.36–7.60 (7H, m), 7.88 (2H, d, J=8.4 Hz), 10.22 (1H, s). IR (KBr) ν: 2967, 1663, 1609 cm$^{-1}$. Anal. for C$_{36}$H$_{44}$IN$_3$O$_2$.H$_2$O: Calcd: C, 62.15; H, 6.66; N, 6.04. Found: C, 61.89; H, 6.30; N, 5.97.

Reference Example 28

In dimethylformamide (5 ml) was dissolved N-(4-((N-3-hydroxypropyl-N-methyl)aminomethyl)phenyl)-2-(4-methylphenyl)-6,7-dihydro-5H-benzocycloheptene-8-carboxamide (0.2 g), and to the mixture was added methyl iodide (0.04 ml). Under nitrogen atmosphere, the mixture was stirred at room temperature overnight. The solvent was evaporated, and to the residue was added ethyl acetate to give crude crystals, which were filtered and recrystallized from ethanol-ethyl acetate to give N-(3-hydroxypropyl)-N,N-dimethyl-(N-(2-(4-methylphenyl)-6,7-dihydro-5H-benzocycloheptene-8-carbonyl)-4-aminobenzyl)ammonium iodide (0.05 g) as colorless crystals.

mp 210–213° C. $^1$H-NMR(CDCl$_3$+CD$_3$OD) δ: 2.00–2.20 (4H, m) , 2.40 (3H, s) , 2.71 (2H, t, J=6.6 Hz), 2.87–2.92 (2H, m), 3.10 (6H, s), 3.54–3.65 (2H, m), 3.73 (2H, t, J=5.3 Hz), 4.63 (2H, s), 7.22–7.27 (3H, m), 7.43–7.58 (7H, m), 7.80 (2H, d, J=8.4 Hz), 9.21 (1H, s). IR (KBr) ν: 3337, 2934, 1653 cm$^{-1}$. Anal. for C$_{31}$H$_{37}$IN$_2$O$_2$.0.5H$_2$O: Calcd: C, 61.49; H, 6.33; N, 4.63. Found: C, 61.55; H, 6.22; N, 4.74.

Reference Example 29

In dimethylformamide (5 ml) was dissolved N-(4-((N-3-hydroxypropyl-N-methyl)aminomethyl)phenyl)-7-(4-methylphenyl)-2,3-dihydro-1-benzoxepine-4-carboxamide (0.14 g), and to the mixture was added methyl iodide (0.04 ml). Under nitrogen atmosphere, the mixture was stirred at room temperature overnight. The solvent was evaporated, and to the residue was added ethyl acetate to give crude crystals, which were filtered and recrystallized from ethanol-ethyl acetate to give dimethyl-3-hydroxypropyl-(N-(7-(4-methylphenyl)-2,3-dihydro-1-benzoxepin-4-carbonyl)-4-aminobenzyl)ammonium iodide (0.15 g) as colorless crystals.

mp 216–219° C. $^1$H-NMR(CDCl$_3$+CD$_3$OD) δ: 2.00–2.20 (2H, m)), 2.40 (3H, s), 3.06–3.10 (2H, m), 3.10 (6H, s), 3.51–3.61 (2H, m), 3.73 (2H, t, J=5.4 Hz), 4.37 (2H, t, J=4.6 Hz), 4.61 (2H, s), 7.07 (1H, d, J=8.4 Hz), 7.25 (2H, d, J=8.2 Hz), 7.46–7.59 (7H, m), 7.81 (2H, d, J=8.2 Hz), 9.54 (1H, s). IR (KBr) ν: 3306, 1651 cm$^{-1}$. Anal. for C$_{30}$H$_{35}$IN$_2$O$_3$.0.5H$_2$O: Calcd: C, 59.31; H, 5.97; N, 4.61. Found: C, 59.36; H, 5.95; N, 4.75.

Reference Example 30

In dimethylformamide (5 ml) was dissolved 7-(4-methylphenyl)-N-(4-((N-tetrahydropyran-4-yl-N-methyl)aminomethyl)-phenyl)-2,3-dihydro-1-benzothiepine-4-carboxamide (0.19 g), and to the mixture was added methyl iodide (0.03 ml). Under nitrogen atmosphere, the mixture was stirred at room temperature overnight. The solvent was evaporated, and to the residue was added ethyl acetate to give crude crystals, which were filtered and recrystallized from ethanol-hexane to give dimethyl-(N-(7-(4-methylphenyl)-2,3-dihydro-1-benzothiepine-4-carbonyl)-4-aminobenzyl)-N-(4-tetrahydropyranyl)ammonium iodide (0.2 g) as colorless crystals.

mp 220–222° C. (dec.). $^1$H-NMR(DMSO-d$_6$) δ: 1.78–1.95 (2H, m), 2.05–2.20 (2H, m), 2.35 (3H, s), 2.88 (6H, s), 2.95–3.05 (2H, m), 3.21–3.32 (4H, m), 3.50–3.65 (1H, m), 4.05–4.15 (2H, m), 4.46 (2H, s), 7.29 (2H, d, J=8.0 Hz), 7.46–7.63 (7H, m), 7.81–7.90 (3H, m), 10.34 (1H, s). IR (KBr) ν: 2924, 1657 cm$^{-1}$.

Reference Example 31

In dimethylformamide (5 ml) was dissolved N-(4-((N-methyl-N-(pentan-3-yl))aminomethyl)phenyl)-2-(4-methylphenyl)-6,7-dihydro-5H-benzocycloheptene-8-carboxamide (0.17 g), and to the mixture was added methyl iodide (0.08 ml). Under nitrogen atmosphere, the mixture was stirred at 45° C. overnight. The solvent was evaporated, and to the residue was added ethyl acetate to give crude crystals, which were filtered and recrystallized from ethanol-ethyl acetate to give dimethyl-(N-(2-(4-methylphenyl)-6,7-dihydro-5H-benzocycloheptene-8-carbonyl)-4-aminobenzyl)-N-(pentan-3-yl)ammonium iodide (0.15 g) as colorless crystals.

mp 190–194° C. (dec.). $^1$H-NMR(CDCl$_3$) δ: 1.15 (6H, t, J=7.4 Hz), 1.67–1.82 (2H, m), 2.05–2.25 (4H, m), 2.39 (3H, s), 2.73 (2H, t, J=6.6 Hz), 2.80–2.90 (2H, m), 3.11 (6H, s), 3.40–3.51 (1H, m), 4.91 (2H, s), 7.18–7.26 (3H, m), 7.44 (1H, dd, J=1.8, 8.4 Hz), 7.49 (2H, d, J=8.4 Hz), 7.57–7.62 (4H, m), 7.80 (2H, d, J=8.4 Hz), 8.35 (1H, s). IR (KBr) ν: 2936, 1659 cm$^{-1}$. Anal. for C$_{33}$H$_{41}$IN$_2$O.0.5H$_2$O: Calcd: C, 64.18; H, 6.85; N, 4.54. Found: C, 63.84; H, 6.73; N, 4.47.

Reference Example 32

In DMF (50 ml) was dissolved N-cyclohexyl-N-methylamine (12.5 g, 0.11 mol), and to the solution were added potassium carbonate (27.6 g, 0.20 mol) and 4-nitrobenzylbromide (21.6 g, 0.10 mol). The mixture was stirred at room temperature for 5 hours. Under reduced pressure, the reaction mixture was concentrated. To the residue was added ethyl acetate, and the mixture was extracted with water. The ethyl acetate layer was washed with saturated sodium chloride solution, dried with MgSO$_4$ and concentrated under reduced pressure. The residue was purified with silica gel column chromatography (ethyl acetate/hexane) to give N-cyclohexyl-N-methyl-N-(4-nitrobenzyl)amine (24.8 g).

$^1$H-NMR (200 MHz, CDCl$_3$) δ: 1.0–1.95 (10H, m), 2.19 (3H, s), 3.66 (2H, s), 7.51 (2H, d, J=8.8 Hz), 8.17 (2H, d, J=8.8 Hz).

Reference Example 33

To a solution of N-cyclohexyl-N-methyl-N-(4-nitrobenzyl)amine (12.4 g, 50.0 mmol) in methanol (250 ml) were added nickel bromide (1.09 g, 5.0 mmol) and then sodium boron hydride (7.57 g, 200 mmol) at 0° C., and the mixture was stirred at room temperature for 30 minutes. To the mixture were added nickel bromide (0.55 g, 2.5 mmol) and then sodium boron hydride (3.78 g, 100 mmol) at 0° C., and the mixture was stirred at room temperature for 30 minutes. To the reaction mixture was added water (100 ml), and the mixture was concentrated under reduced pressure. To the residue was added ethyl acetate, and insoluble material was filtered off with Celite. The filtrate was washed with ethyl acetate, and the ethyl acetate layer was dried with MgSO$_4$ and concentrated under reduced pressure. The residue was washed with hexane to give 4-(N-cyclohexyl-N-methylaminomethyl)aniline (3.99 g, 37%).

$^1$H-NMR (200 MHz, CDCl$_3$) δ: 1.0–1.95 (10H, m), 2.17 (3H, s), 2.3–2.55 (1H, m), 3.46 (2H, s), 3.59 (2H, br s), 6.65 (2H, d, J=8.5 Hz), 7.10 (2H, d, J=8.5 Hz).

Reference Example 34

To a solution of 7-(4-methylphenyl)-2,3-dihydro-1-benzoxepine-4-carboxylic acid (0.28 g), 4-(N-cyclohexyl-N-methylaminomethyl)aniline (0.24 g) and 1-hydroxybenzotriazole (0.15 g) in dimethylformamide (10 ml) was added 1-ethyl-3-(3-dimethylaminopropyl)carbodiimide hydrochloride (0.29 g) under ice-cooling. Under nitrogen atmosphere, the mixture was cooled to room temperature, and to the mixture were added 4-dimethylaminopyridine (3 mg) and triethylamine (0.42 ml). The mixture was stirred for 20 hours, poured into water, and extracted with ethyl acetate. The organic layer was washed with water and saturated sodium chloride solution and dried with anhydrous magnesium sulfate. Under reduced pressure, the solvent was evaporated, and the residue was washed with ethyl acetate and dried to give N-(4-(N-cyclohexyl-N-methylaminomethyl)phenyl)-7-(4-methylphenyl)-2,3-dihydro-1-benzoxepine-4-carboxamide (0.40 g).

$^1$H-NMR (CDCl$_3$) δ: 1.0–1.95 (10H, m), 2.20 (3H, s), 2.35–2.55 (1H, m), 2.40 (3H, s), 3.0–3.15 (2H, m), 3.56 (2H, s), 4.3–4.45 (2H, m), 7.06 (1H, d, J=8.4 Hz), 7.2–7.6 (11H, m).

Reference Example 35

In dimethylformamide (7 ml) was dissolved N-(4-(N-cyclohexyl-N-methylaminomethyl)phenyl)-7-(4-methylphenyl)-2,3-dihydro-1-benzoxepine-4-carboxamide (0.15 g), and to the mixture was added methyl iodide (0.06 ml). Under nitrogen atmosphere, the mixture was stirred at room temperature for 20 hours. The solvent was evaporated, and to the residue was added ethyl acetate to give crude crystals, which were filtered and recrystallized from ethanol to give N-cyclohexyl-N,N-dimethyl-N-((7-(4-methylphenyl)-2,3-dihydro-1-benzoxepin-4-carbonyl)-4-aminobenzyl)ammonium iodide (0.15.g).

$^1$H-NMR(CDCl$_3$) δ: 1.0–1.8 (6H, m), 1.9–2.05 (2H, m), 2.25–2.45 (2H, m), 2.36 (3H, s), 2.95–3.15 (8H, m), 3.45–3.7 (1H, m), 4.2–4.35 (2H, m), 4.83 (2H, s), 6.99 (1H, d, J=8.4 Hz), 7.21 (2H, d, J=7.6 Hz), (6H, m), 7.74 (1H, d, J=2.2 Hz), 7.85 (2H, d, J=8.6 Hz), 8.79 (1H, s). IR (KBr) ν: 1659, 1609, 1593, 1518, 1493 cm$^{-1}$.

Reference Example 36.

In dimethylformamide (5 ml) was dissolved N-(4-(N-methyl-N-(tetrahydropyran-4-yl)aminomethyl)phenyl)-7-(4-morpholino-phenyl)-2,3-dihydro-1-benzoxepine-4-carboxamide (0.20 g), and to the mixture was added methyl iodide (0.03 ml). Under nitrogen atmosphere, the mixture was stirred at room temperature for 32 hours. The solvent was evaporated, and the residue was purified with silica-gel column chromatography (dichloromethane/methanol). The desired fraction was concentrated, and to the residue was added ethyl acetate. Insoluble material was filtered and recrystallized from ethanol to give dimethyl-N-(7-(4-morpholinophenyl)-2,3-dihydro-1-benzoxepin-4-carbonyl)-4-aminobenzyl-N-(4-tetrahydropyranyl)ammonium iodide (0.18 g).

$^1$H-NMR (CDCl$_3$)δ: 1.6–2.0 (2H, m), 2.1–2.3 (2H, m), 2.92 (6H, s), 2.95–3.2 (6H, m), 3.35–3.55 (2H, m), 3.8–3.9 (4H, m), 4.0–4.35 (5H, m), 4.84 (2H, s), 6.85–7.05 (3H, m), 7.35–7.85 (9H, m), 8.92 (1H, s). IR (KBr) ν: 1659, 1609, 1520, 1495 cm$^{-1}$.

Reference Example 37

In tetrahydrofuran(100 ml) was dissolved 1,2-methlenedioxy-4-bromobenzene (24.0 g), and to the mixture was dropwise added n-butyllithium (1.6M hexane solution, 82 ml) at −55° C. or less. The mixture was stirred at −70° C. or less for 30 minutes. The resulting solution was dropwise added to a solution of trimethyl borate (18.6 g) in tetrahydrofuran (50 ml) at −60° C. or less through cannula, and the mixture was stirred at −70° C. or less for 1 hour and then for 2 hours while warming the mixture to room temperature. To the reaction mixture were added 1N hydrochloric acid (130 ml) and diethylether (150 ml), and the organic layer was separated. The organic layer was washed with water and saturated sodium chloride solution and dried with anhydrous magnesium sulfate. Under reduced pressure, the solvent was evaporated. The residue was washed with diisopropylether to give 3,4-methlenedioxyphenyl borate (6.79 g).

$^1$H-NMR(DMSO-d$_6$) δ: 5.99 (2H, s), 6.8–6.95 (1H, m), 7.25–7.45 (2H, m).

Reference Example 38

To a mixture of methyl 7-bromo-2,3-dihydro-1-benzoxepine-4-carboxylate (0.57 g), 3,4-methlenedioxyphenyl borate (0.47 g) and sodium carbonate (0.42 g) were added water (2 ml) and 1,2-dimethoxyethane (12 ml). Under argon atmosphere, the mixture was stirred at room temperature for 30 minutes, and to the mixture was added tetrakistriphenylphosphinepalladium (0.16 g). The mixture was stirred at 80° C. for 14 hours and extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/hexane) to give methyl 7-(3,4-methlenedioxyphenyl)-2,3-dihydro-1-benzoxepine-4-carboxylate (0.43 g).

$^1$H-NMR(CDCl$_3$) δ: 2.95–3.10 (2H, m), 3.83 (3H, s), 4.25–4.35 (2H, m), 6.01 (2H, s), 6.87 (1H, d, J=8.6 Hz), 6.95–7.10 (3H, m), 7.40 (1H, dd, J=8.4, 2.4 Hz), 7.47 (1H, d, J=2.2 Hz), 7.65 (1H, s).

Reference Example 39

To methyl 7-(3,4-methlenedioxyphenyl)-2,3-dihydro-1-benzoxepine-4-carboxylate (0.40 g) were added methanol (5 ml) and 1N sodium hydroxide (3.7 ml), and the mixture was stirred at room temperature for 20 hours. To the mixture was added lN hydrochloric acid (3.7 ml), and the mixture was concentrated under reduced pressure. Precipitate was washed with water and diethylether and dried under reduced pressure to give 7-(3,4-methylene-dioxyphenyl)-2,3-dihydro-1-benzoxepine-4-carboxylic acid (0.32 g).

$^1$H-NMR (DMSO-d$_6$) δ: 2.80–2.95 (2H, m), 4.15–4.35 (2H, m), 6.05 (2H, s), 6.97 (1H, d, J=8.1 Hz), 7.01 (1H, d, J=8.4 Hz), 7.16 (1H, dd, J=8.1, 1.7 Hz), 7.29 (1H, d, J=1.7 Hz), 7.53 (2H, dd, J=8.4, 2.3 Hz), 7.63 (1H, s), 7.74 (1H, d, J=2.3 Hz).

Reference Example 40

To a solution of 7-(3,4-methlenedioxyphenyl)-2,3-dihydro-1-benzoxepine-4-carboxylic acid (0.14 g), 4-(N-methyl-N-(tetrahydropyran-4-yl)aminomethyl)aniline (0.11 g) and 1-hydroxy-benzotriazole (0.15 g) in dimethylformamide (10 ml) was added 1-ethyl-3-(3-dimethylaminopropyl) carbodiimide hydrochloride (0.13 g) under ice-cooling. Under nitrogen atmosphere, the reaction mixture was warmed to room temperature. To the mixture were added 4-dimethylaminopyridine (3 mg) and triethylamine (0.19 ml), and the mixture was stirred for 18 hours, poured into water, and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give 7-(3,4-methlenedioxyphenyl)-4-(N-methyl-N-(tetrahydropyran-4-yl)aminomethyl)phenyl)-2,3-dihydro-1-benzoxepine-4-carboxamide (0.19 g).

$^1$H-NMR (CDCl$_3$) δ: 1.55–1.85 (4H, m), 2.21 (3H, s), 2.55–2.80 (1H, m), 3.00–3.15 (2H, m), 3.30–3.45 (2H, m), 3.58 (2H, s), 3.95–4.15 (2H, m), 4.30–4.45 (2H, m), 6.01 (2H, s), 6.88 (1H, d, J=8.6 Hz), 6.95–7.10 (3H, m), 7.20–7.65 (7H, m). IR (KBr) ν: 1653, 1597, 1514, 1483 cm$^{-1}$.

Reference Example 41

In dimethylformamide (5 ml) was dissolved 7-(3,4-methlenedioxyphenyl)-4-(N-methyl-N-(tetrahydropyran-4-yl)aminomethyl)phenyl)-2,3-dihydro-1-benzoxepine-4-carboxamide (95 mg), and to the mixture was added methyl iodide (0.012 ml). Under nitrogen atmosphere, the mixture was stirred at room temperature for 18 hours. The solvent was evaporated, and to the residue was added ethyl acetate. Insoluble material was filtered and recrystallized from ethanol to give dimethyl-N-(7-(3,4-methylenedioxyphenyl)-2,3-dihydro-1-benzoxepin-4-carbonyl)-4-aminobenzyl-N-(4-tetrahydropyranyl)ammonium iodide (101 mg).

$^1$H-NMR (CDCl$_3$) δ: 1.7–2.0 (2H, m), 2.15–2.3 (2H, m), 2.85–3.1 (8H, m), 3.4–3.55 (2H, m), 4.0–4.35 (5H, m), 4.85 (2H, s), 5.96 (2H, s), 6.81 (1H, d, J=7.8 Hz), 6.9–7.1 (3H, m), 7.25–7.7 (5H, m), 7.83 (2H, d, J=8.2 Hz), 8.89 (1H, s). IR (KBr) ν: 1659, 1609, 1520, 1495 cm$^{-1}$.

Reference Example 42

A mixture of methyl 2-bromo-6,7-dihydro-5H-benzocyclohepten-8-carboxylate (1.0 g) in methanol (25 ml), THF (25 ml) and 1N NaOH (18 ml) was refluxed for 1 hour. The solvent was concentrated, acidified using 1N HCl, and extracted with ethyl acetate. The organic layer was washed with water and brine, and dried over $MgSO_4$. The solvent was evaporated in vacuo to give 2-bromo-6,7-dihydro-5H-benzocyclohepten-8-carboxylic acid (0.95 g) as colorless prisms.

mp 213–215° C. (dec.). $^1$H-NMR (δ ppm, $CDCl_3$) 2.00–2.12 (2H, m), 2.62–2.68 (2H, m), 2.76–2.82 (2H, m), 7.04 (1H, d, J=8.2 Hz), 7.35 (1H, dd, J=2.0, 8.2 Hz), 7.48 (1H, d, J=2.0 Hz), 7.74 (1H, s). IR (KBr) ν: 2932, 1669 $cm^{-1}$. Anal. calcd. for $C_{12}H_{11}BrO_2$: C, 53.96; H, 4.15. Found C, 53.93; H, 4.03.

Reference Example 43

Oxalyl chloride (0.5 ml) and DMF (cat.) were added successively to a solution of 2-bromo-6,7-dihydro-5H-benzocyclohepten-8-carboxylic acid (0.95 g) in THF (20 ml) under ice cooling. The mixture was stirred for 1.5 hours at room temperature, and the solvent was evaporated in vacuo. A solution of the residue in THF (25 ml) was added dropwise to a solution of 4-[[N-methyl-N-(tetrahydropyran-4-yl)amino]methyl]aniline (0.9 g) and triethylamine (1.5 ml) in THF (20 ml) under ice cooling. The reaction mixture was stirred for 1.5 hours at room temperature under nitrogen. The solvent was evaporated in vacuo, water was added to the residue, and the mixture was extracted with ethyl acetate. The organic layer was washed with water and brine, and dried over $MgSO_4$. The solvent was evaporated in vacuo to give 2-bromo-N-[4-[[N-methyl-N-(tetrahydropyran-4-yl)amino]methyl]phenyl]-6,7-dihydro-5H-benzocyclohepten-8-carboxamide(1.55 g) as colorless prisms.

mp 116–121° C. $^1$H-NMR (δ ppm, $CDCl_3$) 1.64–1.77 (4H, m), 2.05–2.18 (2H, m), 2.21 (3H, s), 2.59–2.71 (3H, m), 2.76–2.81 (2H, m), 3.37 (2H, dt, J=3.0, 11.2 Hz), 3.57 (2H, s), 4.01–4.07 (2H, m), 7.04 (1H, d, J=8.0 Hz), 7.22 (1H, s), 7.29–7.35 (3H, m), 7.42 (1H, d, J=1.8 Hz), 7.55 (2H, d, J=8.4 Hz), 7.64 (1H, br). IR (KBr) ν: 3279, 2942, 2845, 1653, 1516 $cm^{-1}$. Anal. calcd. for $C_{25}H_{29}BrN_2O_2$: C, 63.97; H, 6.23; N, 5.97. Found C, 63.67; H, 6.10; N, 5.92.

Reference Example 44

A solution of 4-carboxyphenylboronic acid (2.0 g) and sulfuric acid (0.1 ml) in methanol (50 ml) was refluxed overnight. The reaction mixture was poured into water, and the mixture was extracted with ethyl acetate. The organic layer was washed with water and brine, and dried over $MgSO_4$. The solvent was evaporated in vacuo to give 4-methoxycarbonylphenylboronic acid (1.7 g) as colorless prisms.

$^1$H-NMR(δ ppm, $CDCl_3$+DMSO-$d_6$) 3.92 (3H, s), 6.78 (2H, s), 7.93 (2H, d, J=7.8 Hz), 8.02 (2H, d, J=7.8 Hz). IR(KBr) ν: 3370, 1709 $cm^{-1}$.

Reference Example 45

A mixture of 2-bromo-N-[4-[[N-methyl-N-(tetrahydropyran-4-yl)amino]methyl]phenyl]-6,7-dihydro-5H-benzocyclohepten-8-carboxamide (0.95 g) and 4-methoxycarbonylphenylboronic acid (0.4 g) in 1M potassium carbonate (6 ml), ethanol (6 ml) and toluene (75 ml) was stirred for 30 minutes at room temperature under argon. Tetrakis(triphenylphosphine)palladium(0.12 g) was added to the mixture, and the mixture was refluxed for 6 hours under argon. The reaction mixture was extracted with ethyl acetate. The organic layer was washed with water and brine, and dried over $MgSO_4$. The solvent was evaporated in vacuo. The residue was subjected to a silica gel column chromatography (ethyl acetate/methanol/triethylamine) to give 2-(4-methoxycarbonylphenyl)-N-[4-[[N-methyl-N-(tetrahydropyran-4-yl)amino]methyl]phenyl]-6,7-dihydro-5H-benzocyclohepten-8-carboxamide (0.4 g) as colorless prisms.

mp 176–183° C. $^1$H-NMR(δ ppm, $CDCl_3$) 1.70–1.77 (4H, m), 2.14–2.21 (2H, m), 2.21 (3H, s), 2.60–2.76 (3H, m), 2.88–2.93 (2H, m), 3.37 (2H, dt, J=2.6, 11.0 Hz), 3.57 (2H, s), 3.94 (3H, s), 4.01–4.07 (2H, m), 7.26–7.34 (3H, m), 7.43 (1H, s), 7.49 (1H, dd, J=1.8, 8.0 Hz), 7.54–7.57 (3H, m), 7.58–7.68 (3H, m), 8.11 (2H, d, J=8.4 Hz). IR (KBr) ν: 3281, 2948, 2847, 1721 $cm^{-1}$.

Reference Example 46

A mixture of 2-(4-methoxycarbonylphenyl)-N-[4-[[N-methyl-N-(tetrahydropyran-4-yl)amino]methyl]phenyl]-6,7-dihydro-5H-benzocyclohepten-8-carboxamide (0.25 g) in methanol (25 ml), THF (25 ml) and 1N NaOH (5 ml) was refluxed overnight. The reaction mixture was concentrated, and neutralized using 1N HCl. The precipitate was filtered, washed with water and dried to give 2-(4-carboxyphenyl)-N-[4-[[N-methyl-N-(tetrahydropyran-4-yl)amino]methyl]phenyl]-6,7-dihydro-5H-benzocyclohepten-8-carboxamide (0.21 g) as colorless amorphous.

$^1$H-NMR(δ ppm, DMSO-$d_6$) 1.40–1.74 (4H, m), 2.05 (2H, br), 2.10 (3H, s), 2.60–2.64 (3H, m), 2.84 (2H, br), 3.20–3.27 (2H, m), 3.51 (2H, s), 3.87–3.93 (2H, m), 7.24 (2H, d, J=8.4 Hz), 7.30 (1H, d, J=8.4 Hz), 7.40 (1H, s), 7.52–7.70 (6H, m), 7.93 (2H, d, J=8.0 Hz), 10.06 (1H, s). IR (KBr) ν: 2938, 2845, 1647, 1595, 1518, 1395 $cm^{-1}$.

Reference Example 47

To 2-(4-carboxyphenyl)-N-[4-[[N-methyl-N-(tetrahydropyran-4-yl)amino]methyl]phenyl]-6,7-dihydro-5H-benzocyclohepten-8-carboxamide (0.32 g) was added 1N HCl (2 ml), and the solvent was evaporated in vacuo, and dried. Diphenyldiazomethane (0.4 g) was added to a solution of the residue in DMF (40 ml), and the reaction mixture was heated overnight at 50° C. under nitrogen. The solvent was evaporated in vacuo, and aq. $NaHCO_3$ was added to the residue. The mixture was extracted with ethyl acetate. The organic layer was washed with water and brine, and dried over $MgSO_4$. The solvent was evaporated in vacuo. The residue was subjected to a silica gel column chromatography (ethyl acetate/methanol/triethylamine) to give 2-[4-(diphenylmethoxycarbonyl)phenyl]-N-[4-[[N-methyl-N-(tetrahydropyran-4-yl)amino]methyl]phenyl]-6,7-dihydro-5H-benzocyclohepten-8-carboxamide (0.4 g) as colorless prisms.

$^1$H-NMR (δ ppm, $CDCl_3$) 1.63–1.76 (4H, m), 2.05–2.20 (2H, m), 2.20 (3H, s), 2.55–2.71 (1H, m), 2.71 (2H, t, J=6.4 Hz), 2.85–2.90 (2H, m), 3.36 (2H, dt, J=2.6, 11.0 Hz), 3.57 (2H, s), 4.00–4.06 (2H, m), 7.14 (1H, s), 7.23–7.66 (20H, m), 7.79 (1H, s), 8.19 (2H, d, J=8.4 Hz).

Working Example 1

Production of Compound 1

In aqueous methanol was dissolved N,N-dimethyl-N-(4-(((2-(4-methylphenyl)-6,7-dihydro-5H-benzocyclohepten-8-yl)carbonyl)amino)benzyl)-N-(4-tetrahydropyranyl) ammonium iodide (19 g), and the mixture was subjected to ion exchange resin (DOWEX1-x8, 100–200 mesh, Cl⁻ type)

column, which was eluted with aqueous methanol. The solvent of the desired fractions was evaporated, and to the residue was added acetone to give crude crystals, which were recrystallized from ethanol to give N,N-dimethyl-N-(4-(((2-(4-methylphenyl)-6,7-dihydro-5H-benzocyclohepten-8-yl)carbonyl)amino)benzyl)-N-(4-tetrahydropyranyl)ammonium chloride (10.1 g) as colorless crystals.

mp 226–232° C. (dec.). $^1$H-NMR (CDCl$_3$+CD$_3$OD) δ: 1.80–2.00 (2H, m), 2.07–2.26 (4H, m), 2.39 (3H, s), 2.72 (2H, t, J=6.6 Hz), 2.85–2.91 (2H, m), 3.00 (6H, s), 3.54 (2H, t, J=11.3 Hz), 4.00–4.21 (3H, m), 4.70 (2H, s), 7.21–7.29 (3H, m), 7.42–7.56 (7H, m), 7.81 (2H, d, J=8.4 Hz), 9.06 (1H, s). IR (KBr) ν: 2934, 1655 cm$^{-1}$. Anal. for C$_{33}$H$_{39}$ClN$_2$O$_2$: Calcd: C, 74.62; H, 7.40; N, 5.27; Cl, 6.67. Found: C, 74.35; H, 7.33; N, 5.20; Cl, 6.80.

Working Example 2

Production of Compound 1

To a solution of N-(4-chloromethylphenyl)-2-(4-methylphenyl)-6,7-dihydro-5H-benzocycloheptene-8-carboxamide (9.38 g, 23.3 mmol) in DMF (50 ml) was dropwise added a solution of N,N-dimethyl-N-tetrahydropyran-4-ylamine (4.5 g, 35.0 mmol) in DMF (50 ml). Under nitrogen atmosphere, the mixture was stirred for 23 hours. The solvent was evaporated to give powder, which was washed with acetone and dried. The resulting colorless powder was recrystallized from ethanol to give N,N-dimethyl-N-(4 -(((2-(4-methylphenyl)-6,7-dihydro-5H-benzocyclohepten-8-yl)carbonyl)amino)benzyl)-N-(4-tetrahydropyranyl)ammonium chloride (Compound 1) (10.6 g, 86%) as colorless powder.

Working Example 3

Production of Compound 2

In aqueous acetonitrile was dissolved N,N-dimethyl-N-(((7-(4-methylphenyl)-2,3-dihydro-1-benzoxepin-4-yl) carbonyl)amino)benzyl)-N-(4-oxocyclohexyl)ammonium iodide (22.8 g), and the mixture was subjected to ion exchange resin (DOWEX-SBR, Cl$^-$ type) column, which was eluted with aqueous acetonitrile. The solvent of the desired fractions was evaporated, and the residue was dissolved in water. The mixture was subjected to freeze-drying to give N,N-dimethyl-N-(((7-(4-methylphenyl)-2,3-dihydro-1-benzoxepin-4-yl)carbonyl)amino)benzyl)-N-(4-oxocyclohexyl)ammonium chloride (Compound 2) (16.1 g) as colorless powder.

$^1$H-NMR(DMSO-d$_6$) δ: 2.05–2.25 (2H, m), 2.34 (3H, s), 2.41–2.61 (6H, m), 2.97 (6H, s), 2.97–3.00 (2H, m), 3.75–3.90 (1H, m), 4.30 (2H, t, J=4.4 Hz), 4.57 (2H, s), 7.06 (1H, d, J=8.4 Hz), 7.27 (2H, d, J=7.8 Hz), 7.45 (1H, s), 7.53–7.60 (5H, m), 7.78 (1H, d, J=2.2 Hz), 7.92 (2H, d, J=8.4 Hz), 10.34 (1H, s). IR (KBr) ν: 3025, 2967, 1717, 1655 cm$^{-1}$. Anal. for C$_{33}$H$_{37}$ClN$_2$O$_3$.0.5H$_2$O: Calcd: C, 71.53; H, 6.91; N, 5.06; Cl, 6.40. Found: C, 71.21; H, 6.94; N, 4.94; Cl, 6.24.

Working Example 4

Production of Compound 2

To a solution of N-(4-chloromethylphenyl)-7-(4-methylphenyl)-2,3-dihydro-1-benzoxepine-4-carboxamide (214 mg, 0.530 mmol) in N,N-dimethylformamide (1 ml) was dropwise added a solution of 4-dimethylaminocyclohexanone (112 mg, 0.795 mmol) in N,N-dimethylformamide (1 ml). Under nitrogen atmosphere, the mixture was stirred for 14 hours. The solvent was evaporated to give crude product, which was washed with ether to give N,N-dimethyl-N-(((7-(4-methylphenyl)-2,3-dihydro-1-benzoxepin-4-yl)carbonyl) amino)benzyl)-N-(4-oxocyclohexyl)ammonium chloride (Compound 2) (305 mg) as colorless powder.

Working Example 5

Production of Compound 3

To a solution of N-(4-chloromethylphenyl)-7-(4-ethoxyphenyl)-2,3-dihydro-1-benzoxepine-4-carboxamide (2.38 g) in DMF (20 ml) was added N,N-dimethyl-N-tetrahydropyran-4-ylamine (1.42 g) at room temperature, and the mixture was stirred for 14 hours. To the reaction mixture was added ethyl acetate (100 ml) to precipitate crystals, which were collected by filtration. The crystal was washed with ethyl acetate to give crude product as pale yellow crystals, which were recrystallized from ethanol to give as N-(4-(((7-(4-ethoxyphenyl)-2,3-dihydro-1-benzoxepin-4-yl)carbonyl)amino)benzyl)-N,N-dimethyl-N-(4-tetrahydropyranyl)ammonium chloride (Compound 3) (1.29 g) colorless crystals.

m.p. 200–204° C. $^1$H-NMR (200 MHz, DMSO-d$_6$) δ: 1.35 (3H, t, J=7.0 Hz), 1.75–1.98 (2H, m), 2.06–2.24 (2H, m), 2.88 (6H, s), 2.94–3.05 (2H, m), 3.28–3.43 (2H, m), 3.49–3.69 (1H, m), 3.99–4.13 (2H, m), 4.07 (2H, q, J=7.0 Hz), 4.23–4.35 (2H, m), 4.47 (2H, s), 6.98–7.07 (3H, m), 7.37 (1H, s), 7.50–7.61 (5H, m), 7.72 (1H, d, J=2.2 Hz), 7.87 (2H, d, J=8.4 Hz), 10.22 (1H, s). IR (KBr) ν: 3425, 1647, 1603, 1520, 1489, 1407, 1317, 1294, 1240, 831 cm$^{-1}$ Anal. for C$_{33}$H$_{39}$N$_2$O$_4$Cl Calcd: C, 70.38 ; H, 6.98 ; N, 4.97 ; Cl, 6.30 Found: C, 70.49 ; H, 7.08 ; N, 4.94 ; Cl, 6.19.

Working Example 6

Production of Compound 3

In aqueous methanol was dissolved N-(4-(((7-(4-ethoxyphenyl)-2,3-dihydro-1-benzoxepin-4-yl)carbonyl) amino)benzyl)-N,N-dimethyl-N-(4-tetrahydropyranyl) ammonium iodide (26.6 g), and the mixture was subjected to ion exchange resin (DOWEX-SBR, Cl$^-$ type) column, which was eluted with aqueous methanol. The solvent of the desired fractions was evaporated, and to the residue was added acetone to give crude crystals, which were recrystallized from ethanol to give N-(4-(((7-(4-ethoxyphenyl)-2,3-dihydro-1-benzoxepin-4-yl)carbonyl)amino)benzyl)-N,N-dimethyl-N-(4-tetrahydropyranyl)ammonium chloride (Compound 3) (16.6 g) as colorless crystals.

Working Example 7

Production of Compound 4

A solution of 2-[4-(diphenylmethoxycarbonyl)phenyl]-N-[4-[[N-methyl-N-(tetrahydropyran-4-yl)amino]methyl]phenyl]-6,7-dihydro-5H-benzocyclohepten-8-carboxamide (0.4 g) and methyl iodide (0.15 ml) in DMF (40 ml) was stirred overnight under nitrogen. The solvent was evaporated in vacuo. Ethyl acetate was added to the residue, and the precipitate was filtered, and washed with ethyl acetate. Trifluoroacetic acid (12 ml) was added to a solution of the precipitate in dichloromethane (25 ml), and the reaction mixture was stirred for 2.5 hours at room temperature. The solvent was evaporated in vacuo. Ethyl acetate was added to the residue, and the solvent was evaporated in vacuo. A mixture of the residue in 50% acetonitrile was subjected to an ion exchange column (Dowex SBR, Cl⁻ form, eluted with 50% acetonitrile). The eluate was evaporated in vacuo to give- N-[4-[[[2-(4-carboxyphenyl)-6,7-dihydro-5H-benzocyclohepten-8-yl]carbonyl]amino]benzyl]-N,N-dimethyl-N-(4-tetrahydro-2H-pyranyl)ammonium chloride (Compound 4) (0.23 g) as colorless amorphous.

$^1$H-NMR ($\delta$ ppm, DMSO-$d_6$) 1.80–2.20 (6H, m), 2.65 (2H, t, J=7.2 Hz), 2.80–2.88 (2H, m), 2.88 (6H, s), 3.24–3.40 (2H, m), 3.53–3.65 (1H, m), 4.05–4.10 (2H, m), 4.47 (2H, s), 7.35–7.41 (2H, m), 7.54 (2H, d, J=8.4 Hz), 7.64 (1H, d, J=8.0 Hz), 7.80–7.91 (5H, m), 8.03 (2H, d, J=8.4 Hz), 10.27 (1H, s). IR (KBr) v: 3034–2872, 1696, 1659, 1607, 1593, 1518 cm$^{-1}$. Anal. calcd. for $C_{33}H_{37}ClN_2O_4 \cdot 0.5H_2O$: C, 69.52; H, 6.72; N, 4.91; Cl, 6.22. Found C, 69.19; H, 6.80; N, 5.03; Cl, 6.15.

Industrial Applicability

The compound of the formula (I) of the present invention has potent CCR5 antagonistic activity and can be advantageously used for the treatment or prevention of infectious disease of various HIV in human (e.g. AIDS).

$R^2$, $R^3$ and $R^4$ are independently an optionally substituted aliphatic hydrocarbon group or an optionally substituted alicyclic heterocyclic ring group, or a pro-drug thereof.

2. A compound according to claim 1, wherein $R^2$ and $R^3$ are independently an optionally substituted acyclic hydrocarbon group.

3. A compound according to claim 1, wherein $R^2$ and $R^3$ are independently an optionally substituted alkyl group.

4. A compound according to claim 1, wherein $R^4$ is an optionally substituted alicyclic hydrocarbon group or an optionally substituted alicyclic heterocyclic ring group.

5. A compound according to claim 4, wherein the alicyclic hydrocarbon group is cycloalkyl.

6. A compound according to claim 4, wherein the alicyclic hydrocarbon group is cyclohexyl.

7. A compound according to claim 4, wherein the alicyclic heterocyclic ring group is a saturated alicyclic heterocyclic ring group.

8. A compound according to claim 4, wherein the alicyclic heterocyclic ring group is tetrahydropyranyl, tetrahydrothiopyranyl or piperidyl.

9. N,N-Dimethyl-N-(4-(((2-(4-methylphenyl)-6,7-dihydro-5H-benzocyclohepten-8-yl)carbonyl)amino)benzyl)-N-(4-tetrahydropyranyl)ammonium chloride.

What is claimed is:

1. A compound of the formula:

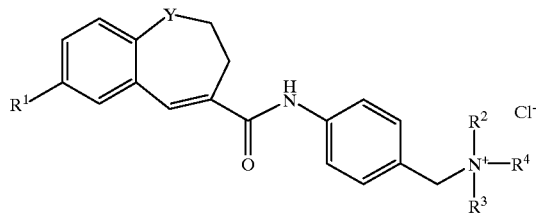

wherein $R^1$ is an optionally substituted phenyl or an optionally substituted thienyl; Y is —CH$_2$—, —S— or —O—; and 10. N,N-Dimethyl-N-(((7-(4-methylphenyl)-2,3-dihydro-1-benzoxepin-4-yl)carbonyl)amino)benzyl)-N-(4-oxocyclohexyl)ammonium chloride.

11. N-(4-(((7-(4-Ethoxyphenyl)-2,3-dihydro-1-benzoxepin-4-yl)carbonyl)amino)benzyl)-N,N-dimethyl-N-(4-tetrahydropyranyl)ammonium chloride.

12. A pharmaceutical composition which comprises a compound as claimed in claim 1.

13. A pharmaceutical composition for antagonizing CCR5 which comprises a compound as claimed in claim 9.

14. A composition according to claim 13, which is for the treatment of infectious disease of HIV.

15. A composition according to claim 13, which is for the treatment of AIDS.

16. A composition according to claim 13, which is for the prevention of the progression of AIDS.

17. A composition according to claim 13, which is used in combination with a protease inhibitor and/or a reverse transcriptase inhibitor.

18. A composition according to claim 17, wherein the reverse transcriptase inhibitor is zidovudine, didanosine, zalcitabine, lamivudine, stavudine, nevirapine, delavirdine, efavirenz or abacavir.

19. A composition according to claim 17, wherein the protease inhibitor is saquinavir, ritonavir, indinavir or nelfinavir.

20. A method for treating the infectious diseases of HIV comprising administering to a mammal in need thereof an effective amount of the compound as claimed in claim 9 in combination with a protease inhibitor and/or a reverse transcriptase inhibitor.

21. A method for manufacturing a medicament for antagonizing CCR5 comprising using the compound as claimed in claim 9.

22. A method for antagonizing CCR5 which comprises administering to a mammal in need thereof an effective amount of the compound as claimed in claim 9.

* * * * *